(12) United States Patent
Grandis et al.

(10) Patent No.: US 10,183,977 B2
(45) Date of Patent: *Jan. 22, 2019

(54) STABILIZED STAT3 DECOY OLIGONUCLEOTIDES AND USES THEREFOR

(71) Applicants: UNIVERSITY OF PITTSBURGH—OF THE COMMONWEALTH SYSTEM OF HIGHER EDUCATION, Pittsburgh, PA (US); CARNEGIE MELLON UNIVERSITY, Pittsburgh, PA (US)

(72) Inventors: Jennifer R. Grandis, Pittsburgh, PA (US); Daniel E. Johnson, Glenshaw, PA (US); Danith Ly, Pittsburgh, PA (US)

(73) Assignees: UNIVERSITY OF PITTSBURGH-OF THE COMMONWEALTH SYSTEM OF HIGHER EDUCATION, Pittsburgh, PA (US); CARNEGIE MELLON UNIVERSITY, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/611,298

(22) Filed: Jun. 1, 2017

(65) Prior Publication Data

US 2018/0134758 A1 May 17, 2018

Related U.S. Application Data

(63) Continuation of application No. 14/739,990, filed on Jun. 15, 2015, which is a continuation of application No. 14/245,911, filed on Apr. 4, 2014, now Pat. No. 9,062,121, which is a continuation of application No. 13/491,343, filed on Jun. 7, 2012, now Pat. No. 8,722,640, which is a continuation of application No. PCT/US2010/061065, filed on Dec. 17, 2010.

(60) Provisional application No. 61/324,649, filed on Apr. 15, 2010, provisional application No. 61/287,341, filed on Dec. 17, 2009.

(51) Int. Cl.
| | |
|---|---|
| C07H 21/02 | (2006.01) |
| C07H 21/04 | (2006.01) |
| A61K 31/70 | (2006.01) |
| C07K 14/47 | (2006.01) |
| A61K 45/06 | (2006.01) |
| C12N 15/113 | (2010.01) |
| C12N 15/115 | (2010.01) |
| A61K 31/713 | (2006.01) |
| A61K 39/395 | (2006.01) |
| A61N 5/00 | (2006.01) |
| C12N 5/00 | (2006.01) |
| A61K 39/00 | (2006.01) |

(52) U.S. Cl.
CPC ............ *C07K 14/47* (2013.01); *A61K 31/713* (2013.01); *A61K 39/39558* (2013.01); *A61K 45/06* (2013.01); *A61N 5/00* (2013.01); *C12N 15/113* (2013.01); *C12N 15/115* (2013.01); *A61K 2039/505* (2013.01); *C12N 2310/13* (2013.01); *C12N 2310/16* (2013.01); *C12N 2310/315* (2013.01); *C12N 2310/3231* (2013.01); *C12N 2310/341* (2013.01); *C12N 2310/531* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 5,139,941 | A | 8/1992 | Muzyczka et al. |
| 5,436,146 | A | 7/1995 | Shenk et al. |
| 5,478,745 | A | 12/1995 | Samulski et al. |
| 5,872,105 | A | 2/1999 | Kool |
| 6,548,048 | B1 | 4/2003 | Cuthbertson et al. |
| 6,548,286 | B1 | 4/2003 | Samulski et al. |
| 6,653,458 | B1 | 11/2003 | Manoharan et al. |
| 6,656,498 | B1 | 12/2003 | Gao |
| 6,696,038 | B1 | 2/2004 | Mahato et al. |
| 6,727,044 | B1 | 4/2004 | Fujimaki et al. |
| 6,743,909 | B2 | 6/2004 | Cowsert et al. |
| 6,749,863 | B1 | 6/2004 | Chang et al. |
| 6,753,423 | B1 | 6/2004 | Cook et al. |
| 6,762,169 | B1 | 7/2004 | Manoharan et al. |
| 7,033,574 | B1 | 4/2006 | Schneider et al. |
| 7,115,583 | B2 | 10/2006 | Porter et al. |
| 7,468,418 | B2 | 12/2008 | Iversen et al. |
| 8,722,640 | B2 | 5/2014 | Grandis et al. |

(Continued)

FOREIGN PATENT DOCUMENTS

| | | |
|---|---|---|
| WO | WO 2006/012625 A2 | 2/2006 |
| WO | WO 2007/013852 A1 | 2/2007 |

OTHER PUBLICATIONS

Crooke, Antisense Drug Technology 2nd Edition, CRC Press 2008, Chapter 19—Locked Nucleic Acid by Troels Koch and Henrik Orum.

(Continued)

*Primary Examiner* — Sean McGarry
(74) *Attorney, Agent, or Firm* — Baker Botts L.L.P.

(57) ABSTRACT

The present invention is based, at least in part, on novel, unimolecular STAT3 oligonucleotide decoys exhibiting increased in vivo stability as compared to previously known decoys which are effective in inhibiting STAT3 when administered systemically. The invention is also based on pharmaceutical compositions comprising these unimolecular decoys, and methods for using these decoys in the treatment of cancer.

20 Claims, 24 Drawing Sheets

Specification includes a Sequence Listing.

(56) References Cited

U.S. PATENT DOCUMENTS

| | | | |
|---|---|---|---|
| 2002/0052333 | A1 | 5/2002 | Dzau et al. |
| 2002/0128217 | A1 | 9/2002 | Dzau et al. |
| 2003/0186922 | A1 | 10/2003 | Dzau et al. |
| 2006/0293264 | A1 | 12/2006 | Grandis et al. |

OTHER PUBLICATIONS

Oliver et al., "In vitro Effects of the BH3 Mimetic, (−)-Gossypol, on Head and Neck Squamous Cell Carcinoma Cells," Clinical Cancer Research 10:7757-7763 (2004).
U.S. Appl. No. 13/491,343, filed Jun. 7, 2012, U.S. Pat. No. 8,722,640, May 13, 2014, Grandis et al.
U.S. Appl. No. 14/245,911, filed Apr. 4, 2014, U.S. Pat. No. 9,062,121, Jun. 23, 2015, Grandis et al.
U.S. Appl. No. 14/739,990, filed Jun. 15, 2015, Abandoned.
U.S. Appl. No. 14/739,990, Jun. 9, 2017 Notice of Abandonment.
U.S. Appl. No. 14/739,990, Dec. 1, 2016 Non-Final Office Action.
U.S. Appl. No. 14/739,990, Nov. 4, 2016 Amendment and Request for Continued Examination (RCE).
U.S. Appl. No. 14/739,990, Oct. 17, 2016 Advisory Action.
U.S. Appl. No. 14/739,990, Oct. 5, 2016 Response after Final Office Action.
U.S. Appl. No. 14/739,990, Aug. 5, 2016 Final Office Action.
U.S. Appl. No. 14/739,990, Jun. 30, 2016 Response to Non-Final Office Action.
U.S. Appl. No. 14/739,990, Feb. 1, 2016 Non-Final Office Action.
U.S. Appl. No. 14/245,911, May 13, 2015 Issue Fee Payment.
U.S. Appl. No. 14/245,911, Feb. 18, 2015 Notice of Allowance.
U.S. Appl. No. 14/245,911, Jan. 16, 2015 Response after Final Action.
U.S. Appl. No. 14/245,911, Jan. 16, 2015 Terminal Disclaimer Filed.
U.S. Appl. No. 14/245,911, Nov. 17, 2014 Final Office Action.
U.S. Appl. No. 14/245,911, Oct. 31, 2014 Response to Non-Final Office Action.
U.S. Appl. No. 14/245,911, Jul. 31, 2014 Non-Final Office Action.
U.S. Appl. No. 13/491,343, Mar. 25, 2014 Issue Fee payment.
U.S. Appl. No. 13/491,343, Jan. 31, 2014 Notice of Allowance.
U.S. Appl. No. 13/491,343, Dec. 5, 2013 Amendment and Request for Continued Examination (RCE).
U.S. Appl. No. 13/491,343, Sep. 6, 2013 Final Office Action.
U.S. Appl. No. 13/491,343, Aug. 7, 2013 Response to Non-Final Office Action.
U.S. Appl. No. 13/491,343, Feb. 8, 2013 Non-Final Office Action.
Antao et al., "Thermodynamic parameters for loop formation in RNA and DNA hairpin tetraloops," Nucleic Acids Res., 20(4):819-824 (1992).
Bowman et al., "STATs in oncogenesis," Oncogene, 19(21):2474-2488 (2000).
Bromberg et al., "Stat3 as an oncogene," Cell, 98(3):295-303 (1999).
Catlett-Falcone et al., "STAT proteins as novel targets for cancer therapy. Signal transducer an activator of transcription," Curr. Opin. Oncol., 11(6):490-496 (1999).
Chan et al., "Disruption of Stat3 reveals a critical role in both the initiation and the promotion stages of epithelial carcinogenesis," J. Clin. Invest., 114(5):720-728 (2004).
Chevrie et al., NAR 18(21):6353-6359 (1990).
Crinelli et al., Nucleic Acids Research, 32(6):1874-1885 (2004).
Darnell, "STATs and gene regulation," Science, 277(5332):1630-1635 (1997).
Di Giusto et al., "Strong positional preference in the interaction of LNA oligonucleotides with DNA polymerase and proofreading exonuclease activities: Implications for genotyping assys," Nucleic Acids Research, 32(3):e32 (2004).
Durand et al., "Circular dichroism studies of an oligodeoxyribonucleotide containing a hairpin loop made of hexaethylene glycol chain: Conformation and stability," Nucleic Acids Res., 18(21):6353-6359 (1990).

El-Sagheer et al., "A very stable cyclic DNA mini duplex with just two base pairs," Chembiochem., 9(1):50-52 (2008).
Fischer et al., "Cellular delivery of impermeable effector molecules in the form of conjugates with peptides capable of mediating membrane translocation," Bioconjugate Chemistry, 12(6):825-841 (2001).
Fry et al., "A specific inhibitor of the epidermal growth factor receptor tyrosine kinase," Science, 265(5175):1093-1095 (1994).
Garcia et al., "Constitutive activation of Stat3 by the Src and JAK tyrosine kinases participates in growth regulation of human breast carcinoma cells," Oncogene, 20(20):2499-2513 (2001).
Gouilleux-Gruart et al., "STAT-related transcription factors are constitutively activated in peripheral blood cells from acute leukemia patients," Blood, 87(5):1692-1697 (1996).
Grandis et al., "Constitutive activation of Stat3 signaling abrogates apoptosis in squamous cell carcinogenesis in vivo," PNAS, 97(8):4227-4237 (2000).
Hawkins et al., "Apoptotic death of pancreatic cancer cells induced by polyunsaturated fatty acids varies with double bond number and involves an oxidative mechanism," Journal of Pathology, 185(1):61-70 (1998).
Hbibi et al., FEBS Journal 276:2505-2515, published online Mar. 16, 2009.
Hirao et al., "Most compact hairpin-turn structure exerted by a short DNA fragment, d (GCGAAGC) in solution: an extraordinary stable structure resistant to nucleases and heat," Nucleic Acids Res., 22(4):576-582 (1994).
Huang et al., "Constitutive activation of Stat 3 oncogene product in human ovarian carcinoma cells," Gynecol Oncol., 79(1):67-73 (2000).
International Search Report and Written Opinion for PCT/US2010/061065, dated Mar. 31, 2011 (Corresponds to U.S. Appl. No. 13/491,343).
Kocalka et al., "Rapid and efficient DNA strand cross-linking by click chemistry," Chembiochem, 9(8):1280-1285 (2008).
Kool et al., Annu. Rev. Biophys. Biomol. Struct 25:1-28 (1996).
Kraker et al., "Biochemical and cellular effects of c-Src kinase-selective pyrido[2,3-d]pyrimidine tyrosine kinase inhibitors," Biochem. Pharmacol., 60(7):885-898 (2000).
Lee et al., "Advantages of the circular dumbbell decoy in gene therapy and studies of gene regulation," Current Drug Targets, 4(8):619-623 (2003).
Leong et al. PNAS 100(7):4138-4143 (2003).
Li et al., "Autocrine-mediated activation of STAT3 correlates with cell proliferation in breast carcinoma lines," J. Biol. Chem., 277(20):17397-17405 (2002).
Malam et al., "Liposomes and nanoparticles: Nanosized vehicles for drug delivery in cancer," Trends Pharmacol., Sci., 30(11):592-599 (2009).
Matsusaki et al., "Functional multilayered capsules for targeting and local drug delivery," Expert Opin. Drug Delivery, 6(11):1207-1217 (2009).
Mayer et al., "Ultrasound targeted microbubble destruction for drug and gene delivery," Expert Opin. Drug Delivery, 5(10):1121-1138 (2008).
Nabel et al., "Site-specific gene expression in vivo by direct gene transfer into the arterial wall," Science, 249(4974):1285-1288 (1990).
Nakajima et al., "A central role for Stat3 in IL_6-induced regulation of growth and differentiation in M1 leukemia cells," The EMBO Journal, 15(14):3651-3658 (1996).
Niu et al., "Constitutive Stat3 activity up-regulates VEGF expression and tumor angiogenesis," Oncogene, 21(13):2000-2008 (2002).
Ojima, "Guided molecular missiles for tumor-targeting chemotherapy-case studies using the second-generation taxoids as warheads," Acc. Chem. Res., 41(1):108-119 (2008).
Osako et al., "Increase in nuclease resistance and incorporation of NF-κB decoy oligodeoxynucleotides by modification of the 3'-terminus," The Journal of Gene Medicine, 9:812-819 (2007).
Phillips et al., "Transforming growth factor-alpha-Pseudomonas exotoxin fusion protein (TGF-alpha-PE38) treatment of subcutaneous and intracranial human glioma and medulloblastoma xenografts in athymic mice," Cancer Research, 54(4):1008-1015 (1994).

(56) References Cited

OTHER PUBLICATIONS

Pit et al., "Ultrasonic drug delivery—A general review," Expert Opinion on Drug Delivery, 1(1):37-56 (2004).

Romano et al., "CD40 and B chronic lymphocytic leukemia cell response to fludarabine: the influence of NF-kappaB/Rel transcription factors on chemotherapy-induced apoptosis," Leuk. Lymphoma, 36(2-4):255-262 (2000).

Sen et al., "First-in-Human trial of STAT3 decoy oligonucleotide in head and neck tumors: Implications for cancer therapy," Cancer Discovery, 2(8):694-705 (2012).

Song et al., "STAT signaling in head and neck cancer," Oncogene, 19(21):2489-2495 (2000).

Souissi et al., "A STAT3-inhibitory hairpin decoy oligodeoxynucleotide discriminates between STAT1 and STAT3 and induces death in a human colon carcinoma cell line," Molecular Cancer, 11:12 pages (2012).

Sun et al., Immunobiology 211:199-209 (2006).

Tomita et al., "Transcription factor decoy oligonucleotide-based therapeutic strategy for renal disease," Clin Exp. Nephrol, 11:7-17 (2007).

Tung et al., "Preparation and applications of peptide-oligonucleotide conjugates," Bioconjugate Chemistry, 11(5):605-618 (2000).

Turkson et al., "Phosphotyrosyl peptides block Stat3-mediated DNA binding activity, gene regulation, and cell transformation," J. Biol. Chem., 276(48):45443-45455 (2001).

Turkson et al., "Requirement for Ras/Rac1-mediated p38 and c-Jun N-terminal kinase signaling in Stat3 transcriptional activity induced by the Src oncoprotein," Mol. Cell Biol., 19(11):7519-7428 (1999).

Wagner et al., "The SIF binding element confers sis/PDGF inducibility onto the c-fos promoter," EMBO J., 9(13):4477-4484 (1990).

Xi et al., Oncogene 24:970-979 (2005).

Yu et al., "Enhanced DNA-binding activity of a Stat3-related protein in cells transformed by the Src oncoprotein," Science, 269(5220):81-83 (1995).

Yu et al., "The stats of cancer—New molecular targets come of age," Nature Reviews Cancer, 4(2):97-105 (2004).

Zhang et al., "Therapeutic effects of STAT3 decoy oligodeoxynucleotide on human lung cancer in xenograft mice," BMC Cancer, 7:149 (2007).

SEQUENCE LISTING

```
<160> NUMBER OF SEQ ID NOS: 31

<210> SEQ ID NO 1
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t or g
<220> FEATURE:
<221> NAME/KEY: modified_base
```

```
<222> LOCATION: (7)..(7)
<223> OTHER INFORMATION: a, c, t or g
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (11)..(11)
<223> OTHER INFORMATION: a, c, t or g
<220> FEATURE:
<221> NAME/KEY: modified_base
<222> LOCATION: (13)..(13)
<223> OTHER INFORMATION: a, c, t or g
<220> FEATURE:
<221> NAME/KEY: modified_base
<222> LOCATION: (16)..(65)
<223> OTHER INFORMATION: a, c, t or g and this region may encompass 0-50
      nucleotides, wherein some or all positions may be absent
<220> FEATURE:
<223> OTHER INFORMATION: see specification as filed for detailed
      description of substitutions and preferred embodiments

<400> SEQUENCE: 1
canttcncnt nantcnnnnn nnnnnnnnnn nnnnnnnnnn nnnnnnnnnn nnnnnnnnnn        60 nnnnn                                                                    65

<210> SEQ ID NO 2
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(50)
<223> OTHER INFORMATION: a, c, t or g and this region may encompass 0-50
      nucleotides, wherein some or all positions may be absent
<220> FEATURE:
<221> NAME/KEY: modified_base
<222> LOCATION: (66)..(115)
<223> OTHER INFORMATION: a, c, t or g and this region may encompass 0-50
      nucleotides, wherein some or all positions may be absent
<220> FEATURE:
<223> OTHER INFORMATION: see specification as filed for detailed
      description of substitutions and preferred embodiments

<400> SEQUENCE: 2
nnnnnnnnnn nnnnnnnnnn nnnnnnnnnn nnnnnnnnnn nnnnnnnnnn catttcccgt        60
aaatcnnnnn nnnnnnnnnn nnnnnnnnnn nnnnnnnnnn nnnnnnnnnn nnnnn            115

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agcttgtcga catttcccgt aaatcgtcga g                                       31

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 4
cagttccctt aaatc                                                          15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatttacggg aaatg                                                          15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
catttccctt aaatc                                                          15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatttaaggg aaatg                                                          15

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctcgacgatt tacgggaaat gtcgacaagc t                                        31

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gatttaaggg aactg                                                          15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
cagttcccgt aaatc                                                       15
```

```
<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gatttacggg aactg                                                       15
```

```
<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
catttcacgt aaatc                                                       15
```

```
<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gatttacgtg aaatg                                                       15
```

```
<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
catttccctt aaatc                                                       15
```

```
<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gatttaaggg aaatg                                                       15
```

```
<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
```
catttcccgt caatc                                                    15

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gattgacggg aaatg                                                    15

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cagttcacgt aaatc                                                    15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gatttacgtg aactg                                                    15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cagttcccgt caatc                                                    15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gattgacggg aactg                                                    15

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
catttcacgt caatc                                                    15

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gattgacgtg aaatg                                                     15

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
catttccctt caatc                                                     15

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gattgaaggg aaatg                                                     15

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cagttcacgt caatc                                                     15

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gattgacgtg aactg                                                     15

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cagttccctt caatc                                                     15

```
<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gattgaaggg aactg                                                    15

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
catttcccgt aaatc                                                    15

<210> SEQ ID NO 31
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(50)
<223> OTHER INFORMATION: a, c, t or g and this region may encompass 0-50
      nucleotides, wherein some or all positions may be absent
<220> FEATURE:
<221> NAME/KEY: modified_base
<222> LOCATION: (53)..(53)
<223> OTHER INFORMATION: a, c, t or g
<220> FEATURE:
<221> NAME/KEY: modified_base
<222> LOCATION: (57)..(57)
<223> OTHER INFORMATION: a, c, t or g
<220> FEATURE:
<221> NAME/KEY: modified_base
<222> LOCATION: (59)..(59)
<223> OTHER INFORMATION: a, c, t or g
<220> FEATURE:
<221> NAME/KEY: modified_base
<222> LOCATION: (61)..(61)
<223> OTHER INFORMATION: a, c, t or g
<220> FEATURE:
<221> NAME/KEY: modified_base
<222> LOCATION: (63)..(63)
<223> OTHER INFORMATION: a, c, t or g
<220> FEATURE:
<221> NAME/KEY: modified_base
<222> LOCATION: (66)..(115)
<223> OTHER INFORMATION: a, c, t or g and this region may encompass 0-50
      nucleotides, wherein some or all positions may be absent
<220> FEATURE:
<223> OTHER INFORMATION: see specification as filed for detailed
      description of substitutions and preferred embodiments
<220> FEATURE:
<223> OTHER INFORMATION: see specification as filed for detailed
      description of substitutions and preferred embodiments

<400> SEQUENCE: 31
nnnnnnnnnn nnnnnnnnnn nnnnnnnnnn nnnnnnnnnn nnnnnnnnnn canttcncnt  60
nantcnnnnn nnnnnnnnnn nnnnnnnnnn nnnnnnnnnn nnnnnnnnnn nnnnn        115
```

STABILIZED STAT3 DECOY OLIGONUCLEOTIDES AND USES THEREFOR

CROSS REFERENCE TO RELATED APPLICATIONS

This application is a continuation of U.S. Ser. No. 14/739,990, filed Jun. 15, 2015, which is a continuation of U.S. Ser. No. 14/245,911, filed Apr. 4, 2014 and now U.S. Pat. No. 9,062,121, which is a continuation of U.S. Ser. No. 13/491,343, filed Jun. 7, 2012 and now U.S. Pat. No. 8,722,640, which is a continuation of International Patent Application No. PCT/US10/061065, filed on Dec. 17, 2010, which claims priority from U.S. Provisional Application Ser. No. 61/287,341, filed Dec. 17, 2009 and 61/324,649, filed Apr. 15, 2010, the contents of each of which are hereby incorporated by reference in their entireties.

GRANT INFORMATION

This invention was made with government support under grant numbers CAA077308 and CA101840 awarded by the National Institutes of Health (NIH). The government has certain rights in the invention.

SEQUENCE LISTING

The specification incorporates by reference the Sequence Listing submitted via EFS on Jun. 1, 2017. Pursuant to 37 C.F.R. § 1.52(e)(5), the Sequence Listing text file, identified as 0723690598CON_SL.txt, is 10,025 bytes was created on Jun. 1, 2017. The Sequence Listing, electronically filed herewith, does not extend beyond the scope of the specification and thus does not contain new matter.

INTRODUCTION

The present invention relates to transcription factor oligonucleotide decoys targeting STAT3, compositions comprising these STAT3 oligonucleotide decoys that are effective in vivo when administered systemically, and methods of use thereof in the treatment of cancer.

BACKGROUND OF THE INVENTION

The family of Signal Transducers and Activators of Transcription (STATs) plays a central role in signaling by numerous cytokines, polypeptide growth factors, and oncoproteins. STATs were initially described in the context of regulating physiologic cell signaling contributing to such diverse processes as differentiation, proliferation, and apoptosis. A number of studies have implicated STAT activation, particularly STAT3, in transformation and tumor progression. Constitutive activation of STAT3 has been detected in many hematopoietic and solid malignancies, including multiple myeloma, leukemias, lymphomas, mycosis fungoides, as well as carcinomas of the prostate, breast, lung, pancreas, ovary and head and neck (Garcia, R., et al., Oncogene, 20: 2499-2513, 2001; Gouilleux-Gruart, V., et al. Blood, 87. 1692-1697, 1996; Grandis, J. R., et al. Proc Natl Acad Sci USA, 97: 4227-4232., 2000; Huang, M., et al. Gynecol Oncol, 79: 67-73, 2000; and Bowman, T., et al. Oncogene, 19(21): 2474-2488, 2000). Upon activation, STAT proteins dimerize and translocate to the nucleus where they regulate gene expression by binding to specific DNA-response elements (Darnell, J. E., Jr., Science, 277: 1630-1635, 1997).

To directly address the role of STAT3 as an oncogene, a constitutively active mutant of STAT3 was generated (STAT3C) and shown to induce transformation of fibroblasts and tumor formation in nude mice (Yu, C. L., et al., Science, 269: 81-83, 1995 and Bromberg, J. F., et al., Cell, 98: 295-303, 1999). In addition to being a point of convergence for numerous oncogenic signaling pathways, STAT3 also participates in cell growth and survival. One of the first indications that STAT3 signaling contributes to malignancy, at least in part by preventing apoptosis, came from studies showing that increased expression of the anti-apoptotic Bcl-2-family gene bcl-xL is dependent on constitutively activated STAT3 in multiple-myeloma cells (Catlett-Falcone, R., et al., Curr. Opin. Oncol. (1999) 11:490-496). Inhibition of STAT3 signaling blocked the expression of Bcl-$_{xL}$ in these tumor cells and sensitized them to FAS-mediated apoptosis (Catlett-Falcone, R., Curr. Opin. Oncol. (1999) 11:490-496). Consistent with these findings, STAT3 activation has been shown to regulate Bcl-$x_L$ expression and apoptosis in a wide range of tumor cells (Grandis, J. et al., Proc Natl Acad Sci USA, 97: 4227-4232, 2000; Bromberg, J. et al., Cell, 98: 295-303, 1999; and Niu, G., et al., Oncogene (2002) 21:2000-2008).

The association of STAT3 activation with transformation and tumor progression suggests that STAT3 is an attractive molecular target for cancer therapy. Several strategies have been used to block the action of STAT proteins, including antisense methods, ectopic expression of dominant-negative mutants (Grandis, J. R., et al., Embo J, 15. 3651-3658, 1996; and Li, L. et al., J Biol Chem, 277: 17397-17405, 2002), inhibition of upstream kinases (Fry, D. et al., Science, 265: 1093-1095, 1994; Kraker, A. J., et al., Biochem Pharmacol, 60: 885-898, 2000; and Turkson, J., et al., Mol Cell Biol, 19: 7519-7528, 1999), and phosphotyrosyl peptides (Turkson, J., et al., J Biol Chem, 276: 45443-45455, 2001).

An alternative approach to target the action of transcription factors, including STAT proteins, involves the use of double-stranded "decoy" oligonucleotides. The double-stranded DNA decoy closely corresponds to the response element within the promoter region of a responsive gene. By achieving a sufficient concentration of decoy in the target cells, the authentic interaction between a transcription factor and its endogenous response element in genomic DNA is impaired, with subsequent modulation of gene expression (U.S. Patent Publication Nos. 2002/0052333, 2002/0128217 and 2003/0186922 and Nabel, E. G., et al., Science, 249: 1285-1288, 1990).

STAT3 decoys that decrease STAT3 activation and inhibit growth of squamous cell carcinoma of the head and neck (SCCHN), but not normal cells, have been previously described, including, for example, in U.S. Patent Publication No. 2006/0293264, and Leong, P. L., et al., Proc Natl Acad Sci USA, 100: 4138-4143, 2003. These decoys, when injected directly into tumors, have been shown to be effective in preclinical cancer models of the skin, breast, and lung and demonstrated cancer-specific growth inhibition (Romano M F, et al. Leuk Lymphoma 2000; 36:255-62; Chan K S, et al. J Clin Invest 2004; 114:720-8; Xi S, et al. Oncogene 2005; 24:970-9; Zhang X, et al. BMC Cancer 2007; 7:149; and Sun Z, et al. Immunobiology 2006; 211:199-209). Systemic administration of decoy would be preferred over local injection, at least in part because some tumors are not sufficiently accessible and some (such as small metastases) may be clinically undetectable. However, previously known STAT3 decoys are rapidly degraded in human serum, rendering their systemic administration inefficient or ineffective. It is therefore desirable, and an object of the present invention, to provide novel STAT3 decoys with enhanced stability that can feasibly be administered systemically.

SUMMARY OF THE INVENTION

The present invention is based, at least in part, on novel, unimolecular STAT3 oligonucleotide decoys exhibiting increased in vivo stability as compared to previously known decoys which are effective in inhibiting STAT3 when administered systemically. The invention is also based on pharmaceutical compositions comprising these unimolecular decoys, and methods for using these decoys in the treatment of cancer.

In one aspect, the invention provides double-stranded STAT3 oligonucleotide decoys, where the decoy comprises an oligonucleotide that binds STAT3, e.g., under physiologic conditions, and is effective in inhibiting growth of a cancer in which STAT3 is activated when administered systemically to a subject, and where the decoy has a serum half-life of greater than about 1.5 hours, 2 hours, 3 hours, 4 hours, 5 hours, 6 hours, 7 hours, 8 hours, 12 hours, 20 hours, 24 hours, or 48 hours. In one embodiment, the decoy has a unimolecular duplex structure. In another embodiment, the decoy comprises at least one phosphorothioated nucleotide.

In one embodiment, the invention provides decoys where the two strands are linked at one end by a hairpin, e.g., a hairpin consisting of about three, four, or five nucleotides. For example, the decoy comprising a hairpin can also comprise at least one phosphorothioated nucleotide at the 5' end of one strand, at least one phosphorothioated nucleotide at the 3' end of the other strand, and at least one nucleotide at either end of the hairpin, which can be phosphorothioated. In another embodiment, the decoy comprising a hairpin comprises three phosphorothioated nucleotides at the 5' end of one strand and three phosphorothioated nucleotides at the 3' end of the other strand, and comprises three phosphorothioated nucleotides at either end of the hairpin.

In another embodiment, the invention provides decoys where the two strands are linked at one end by a carbon spacer, e.g., a 18-atom hexa-ethyleneglycol (C-18) spacer. In still another embodiment, the carbon spacer-containing decoy further comprises three phosphorothioated nucleotides at the 5' end of one strand and three phosphorothioated nucleotides at the 3' end of the other strand.

In yet another embodiment, the decoy comprises at least one locked nucleic acid (LNA) at the 5' end of one strand and at least one LNA at the 3' end of the other strand. In still another embodiment, the two strands are linked at one end, e.g., by a carbon spacer or a hairpin.

The decoys of the invention may also comprise cyclic oligonucleotides. In one embodiment, the two strands of the cyclic decoy are linked by spacers at both ends, for example, C-18 spacers. In another embodiment, the 5' end of the sense strand and the 3' end of the antisense strands are linked with LP1a and LP1b spacers and the 3' end of the sense strand and the 5' end of the antisense strands are linked by an LP2 spacer. In still another embodiment, at least one polyunsaturated fatty acid is covalently linked to the decoy.

In one aspect, the invention provides STAT3 decoys comprising CAN$_1$TTCN$_2$CN$_3$TN$_4$AN$_5$TC-(N$_7$-)$_m$-3', (SEQ ID NO:1), wherein N$_1$, N$_2$, N$_3$, N$_4$ and N$_5$ are A, T, G or C, and one, two, three or all of the following conditions are met: N$_1$, is T; N$_2$ is C; N$_3$ is G, N$_4$ is A and N$_5$ is A, and N$_6$ and N$_7$ are A, T, G or C and n and m are independently 0-50. In one embodiment, N$_2$ is a pyrimidine. In another embodiment, at least two of the following conditions are met: N$_1$, is T; N$_2$ is C; N$_3$ is G, N$_4$ is A and N$_5$ is A. In still another embodiment, at least three of the following conditions are met: N$_1$, is T; N$_2$ is C; N$_3$ is G, N$_4$ is A and N$_5$ is A.

In another aspect, the invention provides derivatives of the STAT3 target sequence: (5'-(N$_6$)$_n$-CATTTCCCG-TAAATC-(N$_7$)$_m$-3', (SEQ ID NO:2), in which N$_6$ and N$_7$ are A, T, G or C and n and m are independently 0-50, containing a single nucleotide insertion, deletion or substitution within the sequence 5'-CATTTCCCGTAAATC-3' (SEQ ID NO:30).

The invention also provides pharmaceutical compositions comprising the STAT3 oligonucleotide decoy described herein and a pharmaceutically acceptable carrier. In one embodiment, the pharmaceutical composition further comprises an anticancer agent. In another embodiment, the pharmaceutical composition is formulated as a parenteral dosage form, e.g., in an intravenous dosage form. In still another embodiment, the pharmaceutical composition is contained within a microbubble.

Another aspect of the invention includes methods of inhibiting growth of a cancer in which STAT3 is activated in a patient, comprising administering to the patient an amount of a STAT3 oligonucleotide decoy of the invention effective to inhibit growth of a cancer in a patient. In one embodiment, the cancer is a squamous cell carcinoma, e.g., squamous cell carcinoma of the head and neck (SSCHN). In another embodiment, the cancer is selected from the group consisting of multiple myeloma, HTLV-1 dependent leukemia, acute myelogenous leukemia, large granular lymphocyte leukemia, lymphoma, EBV-related Burkitt's lymphoma, mycosis fungoides, cutaneous T-cell lymphoma, non-Hodgkins lymphoma, anaplastic large-cell lymphoma, breast cancer, melanoma, ovarian cancer, lung cancer, pancreatic cancer, and prostate cancer.

In still another aspect, the methods of treatment of the invention comprise administering a second anticancer therapy to the patient for the treatment of cancer. For example, the anticancer therapy can include radiation and/or chemotherapy. In another embodiment, the anticancer therapy can include an epidermal growth factor receptor (EGFR) antagonist, e.g., antibody against the epidermal growth factor receptor (EGFR) such as cetuximab or other anticancer therapy.

BRIEF DESCRIPTION OF THE DRAWINGS

(FIG. 7A) Lane 1: undigested parent STAT3 decoy, DN4, DS18, LNA, and LNA-1 as run on a 15% TBE+7 M urea gel, lane 2-12: STAT3 decoy, DN4, DS18, LNA and LNA-1 incubated with mouse serum for various lengths of time. (FIG. 7B) Densitometry data of the parent and modified decoys digested with mouse serum at various time points are expressed as stability levels relative to corresponding control (control=undigested modified or parent decoy). The serum stability assay demonstrated increased resistance of DN4, DS18 and LNA to serum nucleases compared to the parent STAT3 decoy.

DETAILED DESCRIPTION OF THE INVENTION

Figure 1:
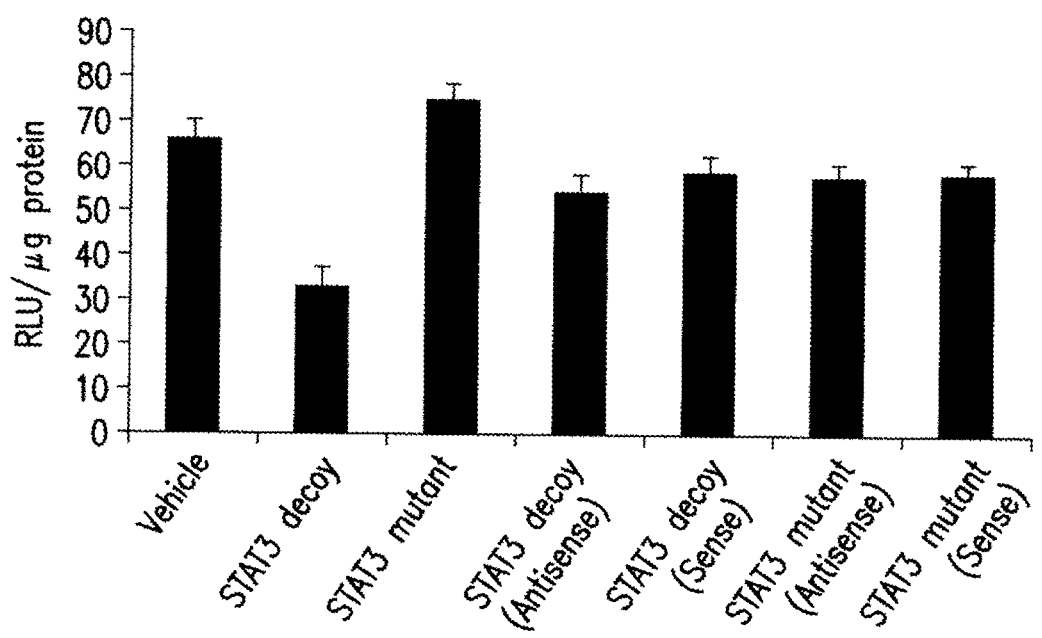
FIG. 1. Depicts the results of a luciferase assay wherein UM-22B cells stably transfected with a luciferase construct under the control of STAT3 hSIE promoter elements were treated with parent STAT3 decoy, STAT3 decoy (sense) and STAT3 decoy (antisense) and their mutant controls at a dose of 12.6 nM for 24 hours in the presence of serum containing media. Luciferase assay was done after 24 hours. Results indicate that the duplex decoy is required to achieve inhibition of STAT3 transcriptional activity.

The present invention is based, at least in part, on novel, STAT3 oligonucleotide decoys that are modifications of previously known decoys and that exhibit increased in vivo stability, and pharmaceutical compositions comprising these decoys. In one embodiment, the STAT3 decoys of the invention have a unimolecular structure. A decoy of the present invention comprises an oligonucleotide that is capable of specifically binding to activated STAT3, e.g., under physiologic conditions, and preventing binding of STAT3 to native response element sequences. The decoys of the invention may be used to inhibit STAT3 activity in vivo and to reduce growth of cancers in which STAT3 is activated, including, but not limited to, SCCHN, breast cancer, lung cancer, skin cancer, prostate cancer, and gliomas. Their enhanced stability makes these decoys amendable to systemic administration.

The present invention is also based, at least in part, on methods comprising encapsulating STAT3 decoys in microbubbles followed by release of the decoys at a tumor site using, for example, therapeutic ultrasound, allowing for systemic administration followed by local delivery of the STAT3 decoy without the need for an intra-tumoral injection. These embodiments enable delivery of decoy to regions that are difficult or dangerous to access by injection (e.g., an intracerebral tumor).

A STAT3 decoy of the present invention can be used alone or in combination with one or more additional cancer therapy known in the art. For example, a STAT3 decoy of the invention can be used in combination with one or more agent that blocks epidermal growth factor receptor (EGFR) expression or activity, including, for example, the monoclonal antibody Cetuximab®, e.g., in the treatment of SCCHN.

STAT3 Decoys of the Invention

As used herein, the terms "decoy" and "transcription factor decoy" refer to molecules that bind to or interact with transcription factors and prevent their binding to native response element sequences. Decoys include nucleic acid sequences, including, but not limited to, oligonucleotides that correspond to (i.e., are identical to or essentially identical to) the native DNA response element.

As used herein, a "STAT3 decoy" comprises a double-stranded deoxyribonucleic acid (DNA) backbone or an analog thereof to which STAT3 binds under physiologic conditions, and which effectively interferes with binding of activated STAT3 to its target DNA sequences in a gene, thereby modulating (changing, altering or otherwise affecting) the effect of activated STAT3 on expression of the gene. A STAT3 decoy can contain any effective sequence, but is defined by its ability to specifically bind STAT3 and to interfere with the binding of STAT3 with its target DNA sequence. As such a STAT3 decoy of the invention contains a "STAT3 target sequence," namely a sequence to which STAT3 binds. For purposes herein, a candidate STAT3 decoy may be tested for its binding affinity and target specificity by electrophoretic mobility shift assay, by binding with STAT3 and by effectively competing with binding of STAT3 to double-stranded DNA comprising a STAT3 target sequence, for example, and without limitation, such as 5'-CAGTTC-CCTTAAATC-3' (SEQ ID NO:4).

In non-limiting embodiments of the invention, a STAT3 decoy comprises a 15-mer double-stranded oligonucleotide backbone, optionally having three phosphorothioate modifications (PTO) at the 3' and/or 5' end of the double-stranded structure (see, for example Leong P L, Andrews G A, Johnson D E, et al. Targeted inhibition of Stat3 with a decoy oligonucleotide abrogates head and neck cancer cell growth. 2003. p. 4138-43; US Patent Application Publication No. 2006/0293264, both of which are incorporated by reference in their entireties herein).

Specific non-limiting examples of STAT3 decoys include (1) an oligonucleotide comprising the STAT3 target sequence 5'-($N_6$)$_n$-CAN$_1$TTCN$_2$CN$_3$TN$_4$AN$_5$TC-($N_7$-)$_m$-3', (SEQ ID NO:1), wherein $N_1$, $N_2$, $N_3$, $N_4$ and $N_5$ are A, T, G or C, and one, two, three or all of the following conditions are met: $N_1$, is T; $N_2$ is C; $N_3$ is G, $N_4$ is A and $N_5$ is A, and $N_6$ and $N_7$ are A, T, G or C and n and m are independently 0-50; (2) the oligonucleotide of (1) where $N_2$ is a pyrimidine; and (3) the DNA or DNA analog of (1) or (2) comprising a derivative of the STAT3 target sequence 5'-($N_6$)$_n$-CATTTC-CCGTAAATC-($N_7$)$_m$-3', (SEQ ID NO:2), in which $N_6$ and $N_7$ are A, T, G or C and n and m are independently 0-50, containing a single nucleotide insertion, deletion or substitution within the sequence 5'-CATTTCCCGTAAATC-3' (SEQ ID NO: 30). By the phrase "containing a single nucleotide insertion, deletion or substituted within the sequence 5'-CATTTCCCGTAAATC-3' (SEQ ID NO: 30)" it is meant that any one of the listed bases may be deleted or substituted, or a nucleotide can be inserted in any place between any of the listed nucleotides. In many instances, two or more nucleotides may be inserted, deleted or substituted within the STAT3 target sequence to produce an effective STAT3 decoy (see Table 1). STAT3 decoy consensus sequences and mutants thereof are described herein and are also known in the art. Wagner et al. also provides mutational analysis and a consensus sequence for the SIF/STAT3 binding domain, Wagner, B. J., et al., EMBO J. 9(13):4477-4484 (1990) (see, FIG. 2). The STAT3 decoy sequence can be repeated two or more times in the STAT3 decoy and/or can be concatamerized or otherwise combined with a second, different decoy sequence.

The STAT3 decoy comprises a double-stranded oligonucleotide or oligonucleotide analog. There is no strict size limit to an "oligonucleotide" or "oligonucleotide analog" as defined herein, only that the oligonucleotide or oligonucleotide analog can pass into a target cell, by itself or with the assistance of a cell permeation enhancer such as a liposome composition or microbubble or a peptide transduction domain, for example, TAT (Fischer, P. M. et al., Bioconjugate Chemistry 12(6):825-841 (2001) and Tung, C. H. et al., Bioconjugate Chemistry 11(5):605-618 (2000)), and provides sufficient sequence information to act as a STAT3 decoy. As such, an oligonucleotide typically ranges from 5 to 100 bases. As an example, certain specific oligonucleotides are, for example, about 5, 10, 11, 12, 13, 14, 15, 16, 17, 18, 19, 20, 25, 30, 35, 40, 45, or 50 bases in length. The term "oligonucleotide", as used herein, may refer to a molecule comprising naturally occurring nucleoside bases or analogs thereof, and/or bases that are not found in nature, such as nucleoside analogs.

As used herein, an "oligonucleotide analog" or "nucleic acid analog" is a nucleic acid, or a nucleic acid substitute, other than a linear, double-stranded DNA, that is a functional analog of a double-stranded DNA, which, in the context of the present disclosure is an effective STAT3 decoy as determined by, for example and without limitation, the electrophoretic mobility shift assays described herein. Functional analogs are compounds that are suitable for use as STAT3 decoys and therefore have adequate sequence specificity and ability to bind to STAT3 and interfere with the binding of STAT3 with its target DNA sequence. Examples of oligonucleotide or nucleic acid analogs include, without limitation: double-stranded RNA, single-stranded DNA and single-stranded RNA. Further non-limiting examples include molecular structures containing oligonucleotide as well as non-nucleic portions, for example a double-stranded oligonucleotide, the strands of which are joined by an organic linker molecule.

The STAT3 decoy may also comprise phosphorothioate (PTO) modifications, e.g., at the 3' and/or 5' ends of the double-stranded structure. For example, in one embodiment (and as referenced in the Examples) the STAT3 decoy comprises three PTO modifications at the 5' and 3' ends of both strands. Other modifications include, without limitation, methylphosphonation.

Other, non-limiting examples of STAT3 decoy modifications include conjugation to a protein/peptide transduction domain, such as TAT; conjugation to cancer cell-targeting peptides, such as ligands of surface proteins expressed or overexpressed on the surface of a target cancer cell, such as without limitation, Epidermal Growth Factor Receptor (see, Phillips, P. C., et al., Cancer Res. 54(4):1008-15 (1994)); methylation; conjugation to tumor-targeting ligands, such as antibodies, folate or iron; cyclization; dumbbell structure and general chemical modification, that is, substitution of one chemical group for another. As an example of a general chemical modification, one group, such as an H, can be substituted with any saturated or unsaturated hydrocarbon group, including lower alkyl ($C_1$-$C_6$), lipid, and polymer (for example, PEG) groups. Examples of modified nucleic acids are provided, without limitation, in U.S. Pat. Nos. 6,653,458, 6,727,044, 6,743,909, 6,753,423 and 6,762,169.

The STAT3 decoy can include nucleotide sequences permitting maintenance of the decoy, either episomally or integrated in the host cell chromosome, in the target cell. Thus, incorporation of one or more STAT3 binding sequences in a plasmid or viral vector can permit a target cell to maintain either transiently or for longer-term the STAT3 decoy as an episome or integrated into a chromosome. Numerous publications and patent documents describe a variety of nucleic acid vectors, plasmids and the like for propagating and maintaining a desired nucleic acid in an episomal or integrated state. In one non-limiting example, a concatamer of a double-stranded DNA STAT3 decoy described herein is inserted between Adeno-Associated Virus (AAV) ITRs according to well-established recombinant methods and is packaged into recombinant AAV (rAAV) virus particles in AAV capsid proteins. The rAAV particles can then be used to infect the target cancer cells, typically, but not exclusively, by intratumoral infection (see, for example, U.S. Pat. Nos. 5,139,941, 5,436,146, 5,478,745 and 6,548,286). Other viral vectors, such as, without limitation, retroviral vectors, are useful in transferring the STAT3 decoy into target cells.

The novel, modified STAT3 decoys of the present invention comprise a STAT3 decoy as set forth above as well as one or more additional modifications that increase stability and/or protect the decoy from degradation when administered systemically, while retaining the ability to bind STAT3, reduce or inhibit growth of a cancer in which STAT3 is activated, interfere with STAT3 binding to a STAT3 response element in cancer cells in which STAT3 is activated, and/or induce apoptosis in tumor cells in which STAT3 is activated.

In non-limiting embodiments, the STAT3 decoys of the present invention comprise chemically-modified DNA strands resulting in a unimolecular structure that retains the ability to bind STAT3 and inhibit tumor cell growth, but substantially maintains a duplex state and exhibits a serum half-life of greater than about 1.5 hours, 2 hours, 3 hours, 4 hours, 5 hours, 6 hours, 7 hours, or 8 hours. A "unimolecular structure" means that the STAT3 decoy, which comprises double-stranded nucleic acid, comprises a feature, which, covalently or non-covalently, promotes duplex formation in at least a portion of the molecule. While not intending to be bound by any particular theory, maintenance of duplex formation in at least a portion of the molecule is believed to be important for STAT3 binding and sequestration. The unimolecular structure is produced using any number of methods, including, but not limited to, linking the two complementary oligonucleotide strands together through a hairpin loop structure, a flexible carbon spacer, or through the use of locked nucleic acid molecules (LNAs). These STAT3 decoys may or may not comprise phosphorothioate modifications at the ends of either or both of the oligonucleotide strands. In certain non-limiting embodiments of the invention, the unimolecular STAT3 decoy is cyclic, thereby promoting double-stranded structure in at least a portion of the molecule.

In one embodiment, the STAT3 decoys of the present invention have a unimolecular structure, retain the ability to bind STAT3 and inhibit tumor cell growth, and/or substantially maintain a duplex state and exhibit a serum half-life of greater than about 1.5 hours, 2 hours, 3 hours, 4 hours, 5 hours, 6 hours, 7 hours, or 8 hours.

As used herein, the term "duplex," in reference to oligonucleotides, refers to regions that are double stranded through hybridization of complementary base pairs. The unimolecular duplex structure can be produced by, for example, covalently linking the two complementary strands together, for example, by introducing a hairpin loop structure or a chemical linker (which may be a nucleic acid or a non-nucleic acid element such as a carbon chain). The term "hairpin" refers to double-stranded nucleic acid structures formed by base-pairing between regions of the same strand of a nucleic acid molecule. The regions are arranged inversely and can be adjacent or separated by noncomplementary sequence.

In one embodiment, the modified STAT3 decoy comprises a 15-mer oligonucleotide with three phosphorothioate modifications at the 5' end of one strand and 3' end of the other wherein the two strands are linked at one end by a hairpin consisting of four nucleotides (e.g., GAAA). The hairpin is not limited to just GAAA, it can be any other sequence with sufficient flexibility that would allow the two halves of the DNA elements to hybridize with one another to form an intramolecular duplex. Nucleotides at either end of the hairpin may be phosphorothioated to confer resistance to S1 nucleases in the hairpin loop structure and increase the stability of the double stranded structure. A decoy comprising this structure is exemplified in the Examples section and FIG. 4 as STAT3 decoy "DN4."

In another embodiment, a non-nucleic acid synthetic spacer, such as, for example, an ethylene glycol spacer having about 12, 13, 14, 15, 16, 17, 18, 20, 21, 22, 23, or 24 carbons may be introduced into the decoy, thereby linking the two oligonucleotide strands. Such carbon spacers are structurally different from the DNA backbone, and do not physically interact with any DNA or with DNA binding enzymes, and therefore protect the decoy from nucleases (Durand M, et al. Nucleic acids res, 1990; 18:6353-9). In one embodiment, a modified STAT3 decoy comprises a 15-mer oligonucleotide with three phosphorothioate modifications at the 5' and 3' end of both the strands, and a C-18 spacer. An example of a decoy comprising this structure is provided in the Examples section and FIG. 5A-B as STAT3 decoy "DS18."

Alternatively, a unimolecular duplex structure may be produced non-covalently by introducing structures which favor base-pairing and increase the melting point of the duplex; in such embodiments, the unimolecular nature of the decoy may be destroyed by conditions that disrupt annealing between base pairs (such as elevated heat), but such conditions would be outside the physiologic range and accordingly would not be expected to be encountered in vivo.

In a non-limiting subset of such non-covalently bound unimolecular STAT3 decoys, modified STAT3 decoys of the invention may contain one or more locked nucleic acid molecules (LNAs). LNAs are a class of nucleic acid analogues in which the ribose ring is "locked" by a methylene bridge connecting the 2'-O atom and the 4'-C atom. LNA oligonucleotides display unprecedented hybridization affinity toward double-stranded DNA (Crooke, Antisense Drug Technology, CRC Press 2008, Chapter 19). Inclusion of even a single LNA induces conformational changes in the sugar pucker of adjacent nucleotides that favor high affinity hybridization. (Id.) The substitution of nucleotide with LNA in an oligonucleotide has been documented and LNAs have displayed high resistance to exo- and endonucleases and result in increased thermal stability of duplex oligonucleotides (Crinelli R, et at Nucleic acids research 2004; 32(6): 1874-85). The decoys of the present invention may contain one or more LNAs positioned at the 5' and/or 3' ends of the oligonucleotide strands. The LNAs should be positioned in a manner that does not interfere with affinity of the decoy molecule by, for example, effecting a conformational change in the binding region. In one exemplary embodiment, the decoys of the invention comprise at least one LNA as well as a spacer or hairpin to form a duplex oligonucleotide.

For example, a modified STAT3 decoy of the present invention comprises an oligonucleotide with one LNA at the 5' end of one strand and 3' end of the other. The two strands are linked at one end by a hairpin consisting of C-18 spacer. An example of this exemplary modified STAT3 decoy is described in the Examples section and FIG. 9 as "LNA-1."

The STAT3 decoys of the invention may also be covalently rendered unimolecular by circularization of the oligonucleotide. Cyclic oligonucleotides have been shown to have potential for biological uses (Kool E T. Annual review of biophysics and biomolecular structure 1996; 25:1-28). They have increased thermodynamic stability potentially arising from the intramolecular nature of the construct (El-Sagheer A H, et al. Chembiochem 2008; 9(1):50-2). In addition, because of their circular nature, they may be more resistant to nuclease degradation in biological media (Lee I K, et al. Current drug targets 2003; 4(8):619-23). As a unimolecular system, duplex formation will be independent of concentration. In one embodiment, the circularized decoy will also contain a spacer or linker at one or both ends linking the two strands. For example, LP1a and LPIb spacers, as described by El-Sagheer et al. (Chembiochem 2008; 9(1):50-2)), or C-18 spacers may be utilized. LP2 may also be used to link the two strands together (Lee and Lee. Curr. Drug Targets 2003; 4(8):619-23). In another embodiment, T1 with DHA attached may be used to link the two strands together (Ojima, et al. Acc. Chem. Res 2008; 41(1): 108-19. Exemplary circularized decoys are set forth in the Examples section, i.e., the "2-CS18," "2 LP," and "2LP DHA" STAT3 decoys, FIGS. 14, 15A-B, and 16A-B.

Maximum efficacy of a systemically delivered STAT3 decoy to the target tumor site requires uptake by the tumor cells. In order to enhance uptake of the STAT3 decoys of the invention into tumor cells when administered systemically, polyunsaturated fatty acids (PUFAs) can be attached to the cyclic STAT3 decoy. The PUFAs can be covalently attached to the cyclic STAT3 decoy. Since PUFAs are a natural source in vegetable oils, cold-water fish, and meat, their application in the delivery of compounds is considered nontoxic for human use. PUFAs exhibit anticancer activity against several different cancer cell lines including Mia-Pa-Ca-2 pancreatic and HL-60 leukemia cell lines; and their antitumor activities have been tested in preclinical and clinical studies (Hawkins R A, Sangster K, Arends M J. The Journal of pathology 1998; 185(1):61-70). Docosahexanoic acid (DHA), an omega-3 polyunsaturated fatty acid, has been classified as a nutritional additive by the FDA (safe for human use). DHA has been effectively used to deliver taxol into cancer cells (Ojima I. Accounts of chemical research 2008; 41(1):108-19).

Pharmaceutical Compositions

The STAT3 decoys of the invention can be incorporated into pharmaceutical compositions suitable for administration to a patient. Such pharmaceutical compositions may further comprise a "pharmaceutical carrier" or "carrier" which may be any compound or composition useful in facilitating storage, stability, administration, cell targeting and/or delivery of the STAT3 decoy to a target cell or cell population, including, without limitation, suitable vehicles, diluents, solvents, excipients, pH modifiers, salts, colorants, flavorings, rheology modifiers, lubricants, coatings, fillers, antifoaming agents, erodible polymers, hydrogels, surfactants, emulsifiers, adjuvants, preservatives, phospholipids, fatty acids, mono- di- and tri-glycerides and derivates thereof, waxes, oils, antibacterial and antifungal agents, isotonic and absorption delaying agents, water, and the like, that are compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one embodiment, the STAT3 decoy is suspended in water (USP) for delivery in vivo. Pharmaceutically acceptable salts, buffers or buffer systems, including, without limitation, saline, phosphate buffer or phosphate buffered saline (PBS) may be included in the dosage form. Vehicles having the ability to facilitate delivery of nucleic acids and/or nucleic acid analogs to a cell in vivo may be utilized to facilitate delivery of the decoy to the target cells. In one embodiment, the decoys are prepared with carriers or vehicles that will protect them against rapid degradation and elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. One non-limiting example of such a vehicle is a liposomal suspension, e.g., a cationic liposome system or liposomal suspension, for example and without limitation as shown in U.S. Pat. Nos. 6,656,498, 6,696,038, 6,749,863, and 4,522,811. Additional vehicles having the ability to facilitate delivery of nucleic acids and/or nucleic acid analogs to a cell in vivo, such as the AAV and retroviral vehicles described above, are suited for use in a STAT3 decoy-containing dosage form.

A pharmaceutical composition of the invention is formulated to be compatible with its intended route of administration. In one embodiment, the STAT3 decoy is delivered intratumorally, which includes delivery internal to a tumor and/or immediately adjacent to a tumor or a cancer cell such that the decoy diffuses to contact the tumor or cancer cell.

The STAT3 decoy also may be administered locally, regionally or systemically as desired, for example and without limitation: intravenously, intramuscularly, subcutaneously, dermally, subdermally, intraperitoneally, transdermally, iontophoretically, orally (e.g., inhalation), and transmucosally. Non-limiting examples of devices useful in delivering the STAT3-containing dosage to a patient include needle/syringes, catheters, trocars, stents or projectiles.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL. (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Depending on the route of administration, varying amounts of the STAT3 decoy may be necessary. The data obtained from in vitro cell-based assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

Although certain threshold amounts of STAT3 decoy need to be delivered by any given dosage form by any given route, each dosage form has differing ability to deliver the decoy to the cancer cells. Typically, intratumoral injection of the STAT3 decoy will require the least amounts of the decoy. Intravenous, or intramuscular systemic delivery typically will require larger amounts of decoy. Dosage forms that efficiently deliver the decoy to a cell would require less decoy than those that are less efficient. Further, certain cancers will require varying amounts of decoy. Therefore, it is more critical that an effective amount of the STAT3 decoy be delivered to a patient in order to achieve a desired therapeutic goal (e.g., reducing or inhibiting growth of a cancer in which STAT3 is activated, interfering with STAT3 binding to a STAT3 response element in cancer cells in which STAT3 is activated, and/or inducing apoptosis in tumor cells in which STAT3 is activated), rather than a fixed dose for every patient. Nevertheless, standard dosage regimens may be developed.

For example, and without limitation, for intratumoral or systemic (e.g., intravenous, intramuscular, subcutaneous, dermal, subdermal, intraperitoneal, transdermal, or transmucosal) delivery of a STAT3 decoy, about 1 to 1,000 µg, typically in 0.1 µg and 1.0 µg increments, of decoy in a carrier may be injected at the tumor site or systemically once daily, every other day, weekly, bi-weekly, monthly, bi-monthly, or otherwise as needed. Depending on the progression of the cancer in the individual patient, one or more intratumoral injections may be needed to ensure sufficient contact of the decoy with the cancer cells. The delivered amounts may range between about 1 and 1,000 µg, including, without limitation, about 1, 2, 3, 4, 5, 10, 15, 20, 25, 50, 100, 250, 500 and 1000 µg, and even higher or lower, as is effective to reach the desired end point, such as, without limitation, reducing or inhibiting growth of a cancer in which STAT3 is activated, interfering with STAT3 binding to a STAT3 response element in cancer cells in which STAT3 is activated, and/or inducing apoptosis in tumor cells in which STAT3 is activated. Intratumoral delivery may, in some instances, require less STAT3 decoy than systemic delivery, for example about 10 to 1,000 µg.

The pharmaceutical compositions can be included in a kit, container, pack, or dispenser together with instructions for administration.

Methods of Treatment

The compositions, methods and articles of manufacture described herein are effective in treating cancers in which STAT3 is activated. Without limitation, one class of cancers that belong to this group is the squamous cell carcinomas, which also are known as epitheloid cancers. As used herein a "squamous cell carcinoma" is a cancer arising, at least in part, from a squamous cell population and/or containing, at least in part, a squamous cell population including, without limitation, certain cancers of the cervix; penis; head and neck, including, without limitation cancers of the oral cavity, salivary glands, paranasal sinuses and nasal cavity, pharynx and larynx; lung; esophageal; skin; vulva and bladder. Other, non-limiting examples of cancers in which STAT3 may be activated are: multiple myeloma; HTLV-1 dependent leukemia; acute myelogenous leukemia (AML); large granular lymphocyte leukemia; lymphomas, including EBV-related Burkitt's lymphoma, mycosis fingoides, cutaneous T-cell lymphoma, non-Hodgkins lymphoma; anaplastic large-cell lymphoma (ALCL), breast cancer, melanoma, ovarian cancer, lung cancer, pancreatic cancer and prostate cancer (Yu, H. et al., Nat. Rev. Cancer, 2004 February, 4(2):97-105). Methods that are known in the art and described in, for example, Song and Grandis, Oncogene, 2000, 19(21):2489, can be used to determine if STAT3 is activated.

Microbubbles can also be used to effectively deliver the STAT3 decoys of the invention when administered systemically. In one embodiment, the decoys are incorporated into or complexed with gas microbubbles which may be in the form of encapsulated gas microspheres or gas bubbles stabilized by materials such as surfactants, lipids, proteins, lipoproteins, and polymers. The gas may be comprised of any species of gas, but physiologically compatible gases such as air and nitrogen are preferred. Microbubbles serve to protect the decoy from degradation until it reaches the tumor, but do not inhibit the ability of the decoy to bind STAT3. The microbubbles comprising the STAT3 decoys of the invention may be delivered into the tumor using high injection pressure, ultrasound treatment of the target tumor, or combinations of ultrasound treatment and injection pressure. Delivery of drugs in microbubbles is described in, for example, Mayer C R, et al. Expert Opin Drug Deliv 2008; 5:1121-38; Pit et al. Expert Opin Drug Deliv. 2004, 1(1): 37, and U.S. Pat. Nos. 7,468,418, 7,033,574, 6,548,048, 7,115,583, incorporated herein by reference. For example, the therapeutic agent (decoy) is trapped in the membrane of the microbubble. Under ultrasound resonances that match the subresonance frequency of the microbubble, the membrane begins to oscillate. At higher ultrasound pressures, the amplitude of the oscillation may be increased to an extent that results in microbubble disruption releasing the drug locally. SCCHN is largely a local-regional disease and head and neck tumors are generally accessible to ultrasound imaging, and are therefore accessible for ultrasound delivery of microbubbles containing the decoys of the invention.

Nano-scale delivery vehicles can also be used to deliver the STAT3 decoys of the present invention. Exemplary methods of drug delivery using nanoparticles are described in, for example, Malam, Y., et al. *Trends Pharmacol. Sci.* 2009 November; 30(11):592-9 and Matsusaki et al. Expert Opin Drug Deliv. 2009 November; 6(11):1207-17, the contents of which are incorporated by reference herein, in their entireties.

Treatment of a patient with the described STAT3 decoy may be combined with other anti-cancer therapies, such as treatment with an anticancer agent and radiation therapy. These therapies can be administered to a patient according to any effective protocol, though the treatments may be modified to optimize the combination treatment along with the STAT3 decoy. For example, and without limitation, radiation therapy is performed by administering to the patient a suitable radiation dose of a suitable time at any suitable interval according to well-established protocols. Anticancer agents are administered according to typical protocols for the given drug. Non-limiting classes of drugs useful in combination with the STAT3 decoy include: tyrosine kinase inhibitors, such as gefitinib (Iressa™) and imatinib mesylate (Gleevec™), monoclonal antibodies, such as rituximab (Rituxan™) and cetuximab (Erbitux™); angiogenesis inhibitors, such as endostatin; immune modulators, such as interleukin-12 (IL-12) and interleukin-2 (IL-2); non-receptor tyrosine kinase inhibitors, such AG490 JAK2 inhibitor and PP2 src family kinase inhibitor or dasatinib; serine/threonine kinase inhibitors, such as UO126 for MEK1/2, wortmanin for PI3K; farnesyl or geranyl transferase inhibitors, such as FTI-277 and GGTI-298; and G-protein-coupled receptor inhibitors, such as RC3095 for bombesin and An-238 for somatostatin.

Non-limiting examples of anticancer agents include: AG-490; aldesleukin; alemtuzumab; alitretinoin; allopurinol; altretamine; amifostine; An-238; anastrozole; arsenic trioxide; asparaginase; BCG Live (*Bacillus* Calmette-Guerin); bevazizumab; bexarotene; bleomycin; busulfan; calusterone; capecitabine; capecitabine; carboplatin; carmustine; celecoxib; cetuximab; chlorambucil; cisplatin; cladribine; cyclophosphamide; cyclophosphamide; cytarabine; dactinomycin; darbepoetin alfa; dasatinib; daunorubicin; daunorubicin, daunomycin; denileukin diftitox; dexrazoxane; docetaxel; doxorubicin; dromostanolone propionate; Elliott's B Solution; endostatin; epirubicin; epoetin alfa; estramustine; etoposide phosphate; etoposide, VP-16; exemestane; filgrastim; floxuridine; fludarabine; fluorouracil; FTI-2777; fulvestrant; gefitinib; gemcitabine; gemcitabine; gerntuzumab ozogamicin; GGTI-298; goserelin acetate; gossypol; hydroxyurea; ibritumomab; idarubicin; idarubicin; ifosfamide; imatinib mesylate; interferon alfa-2a; interferon alfa-2b; IL-2; IL-12; irinotecan; letrozole; leucovorin; levamisole; lomustine; meclorethamine; nitrogen mustard; megestrol acetate; melphalan, L-PAM; mercaptopurine, 6-MP; mesna; methotrexate; methoxsalen; mitomycin C; mitotane; mitoxantrone; nandrolone phenpropionate; nofetumomab; oprelvekin; oxaliplatin; paclitaxel; pamidronate; pegademase; pegaspargase; pegfilgrastim; pentostatin; pentostatin; pipobroman; plicamycin; mithramycin; porfimer sodium; PP2; procarbazine; quinacrine; rasburicase; RC3095; rituximab; sargramostim; streptozocin; talc; tamoxifen; temozolomide; teniposide, VM-26; testolactone; thioguanine, 6-TG; thiotepa; topotecan; toremifene; tositumomab; trastuzumab; tretinoin, ATRA; UO126; uracil mustard; valrubicin; vinblastine; vincristine; vinorelbine; wortmanin; and zoledronate.

A combined dosage form includes an amount of STAT3 decoy and an amount of an anticancer agent effective to reduce growth of a cancer in which STAT3 is activated in a patient, interfere with STAT3 binding to a STAT3 response element in cancer cells of a patient in which STAT3 is activated, and/or induce apoptosis in cancer cells of a patient in which STAT3 is activated. The combined dosage form can be delivered intratumorally, intraperitoneally or intravenously, as is desired.

In one example, the anticancer agent is gossypol (2,2'-bis-(Formyl-1,6,7-trihydroxy-5-isopropyl-3-methylnaphthalene), a drug refined from cottonseed oil and having purported anticancer effects. Gossypol is a BH3 domain small molecule mimetic that targets Bcl-$X_L$. Studies have shown that gossypol binds to the BH3 domain of Bcl-$X_L$ and Bcl-2 to cause apoptosis. Gossypol treatment typically induces DNA fragmentation, PARP cleavage, loss of mitochondrial membrane potential, cytochrome c release, and activation of caspase-3, and -9. Because over-expression of Bcl-$X_L$ has been reported in SCCHN and reduced expression is associated with increased response to chemotherapy, the use of molecular approaches that target Bcl-$X_L$ represents a potential approach to induce apoptosis in SCCHN. Indeed, (−)-gossypol has been shown to be an effective antitumor treatment in SCCHN (Oliver et al., Clin. Cancer Res., 10(22):7757-63, Nov. 15, 2004), but at relatively high concentrations. Gossypol exists in two optical isomers, the (−)-isomer being associated with contraceptive effects, while the (+)-isomer has been implicated in cardiotoxicity in cattle. In one embodiment, the anticancer agent is (−)-gossypol, a composition, which may contain small or trace amounts, and in any case, pharmacologically-insignificant amounts of the (+)-gossypol isomer. A method of resolving a racemic gossypol acetic acid composition into the (+) and (−) enantiomers is provided in Oliver et. al. 2004.

The following examples are intended to further illustrate the invention, without intending for the invention to be limited to the specific embodiments described therein.

Example 1: Parent STAT3 Decoy and Mutant Control Decoys

The parent STAT3 and mutant control decoys, phosphorothioated sense and antisense strands of STAT3 decoy and mutant control decoy oligonucleotides were designed and obtained from DNA Synthesis Facility, University of Pittsburgh (Pittsburgh, Pa.) by means of β-cyanothylphysphoramidite chemistry to minimize degradation of the oligonucleotides by endogenous nucleases. The STAT3 decoy sequence, based on the hSIE sequence, was 5'-CATTTC-CCGTAAATC-3' (SEQ ID NO: 30), 3'-GTAAAGGGCATT-TAG-5' (SEQ ID NO:5) and the mutant control decoy sequence was 5'-CATTTCCCTTAAATC-3'(SEQ ID NO:6), 3'-GTAAAGGGAATTTAG-5' (SEQ ID NO:7). Sense and antisense strands were dissolved in Tris-EDTA (pH 8.0) at a concentration of 900-1,200 µM. Each sense-antisense pair was annealed by heating to 90° C. and decreasing the temperature by 5° C. increments every 15 minutes. After 3 hours, the reaction mixture was held at a base temperature of 4° C.

The STAT3 decoy sequence was systematically derived from the sequence of the c-fos gene shown to be necessary for binding of the sis-inducible factor (SIF) as described in Wagner et al., EMBO J. 9(13):4477-4484 (1990). A longer sequence was initially examined, with the shorter decoy sequence identified by underlining as follows:

(SEQ ID NO: 3)
5'-AGCTTGTCGACATTTCCCGTAAATCGTCGAG-3'

(SEQ ID NO: 8)
3'-TCGAACAGCTGTAAAGGGCATTTAGCAGCTC-5'

Using electrophoretic mobility shift assays (EMSAs), it was found that this longer sequence was effective in blocking STAT3 activation. The decoy sequence was systematically shortened, to the sequence underlined, based on the hypothesis that a smaller decoy would be more likely to enter the cell and demonstrate biologic activity.

Derivative decoys were identified by electrophoretic mobility shift assay.

Table 1 describes a number of STAT3 decoy derivatives along with their relative binding to STAT3.

TABLE 1

Sequences and Relative STAT3-DNA Binding Affinities of STAT3 Decoy and Mutant Decoys.

|  | mutations | # of basepair to STAT3 | Relative binding |
|---|---|---|---|
| STAT3 Decoy (hSIE) (SEQ ID NOS: 30, 5) | 5'-CATTTCCCGTAAATC-3' 3'-GTAAAGGGCATTTAG-5' |  | ++++ |
| SIE (SEQ ID NOS: 4, 9) | 5'-CAGTICCCTTAAATC-3' 3'-GTCAAGGGAATTTAG-5' |  | ++ |
| Mutants of STAT3 Decoy |  |  |  |
| Mutant 1 (SEQ ID NOS: 10, 11) | 5'-CAGTTCCCGTAAATC-3' 3'-GTCAAGGGCATTTAG-5' | 1 | +++ |
| Mutant 2 (SEQ ID NOS: 12, 13) | 5'-CATTTCACGTAAATC-3' 3'-GTAAAGTGCATTTAG-5' | 1 | + |
| Mutant 3 (SEQ ID NOS: 14, 15) | 5'-CATTTCCCTTAAATC-3' 3'-GTAAAGGGAATTTAG-5' | 1 | - |
| Mutant 4 (SEQ ID NOS: 16, 17) | 5'-CATTTCCCGTCAATC-3' 3'-GTAAAGGGCAGTTAG-5' | 1 | ++ |
| Mutant 5 (SEQ ID NOS: 18, 19) | 5'-CAGITCACGTAAATC-3' 3'-GTCAAGTGCATTTAG-5' | 2 | ++ |
| Mutant 6* (SEQ ID NOS: 20, 21) | 5'-CAGTTCCCGTCAATC-3' 3'-GTCAAGGGCAGTTAG-5' | 2 | + |
| Mutant 7 (SEQ ID NOS: 22, 23) | 5'-CATTTCACGTCAATC-3' 3'-GTAAAGTGCAGTTAG-5' | 2 | + |
| Mutant 8 (SEQ ID NOS: 24, 25) | 5'-CATTTCCCTTCAATC-3' 3'-GTAAAGGGAAGTTAG-5' | 2 | +++ |
| Mutant 9 (SEQ ID NOS: 26, 27) | 5'-CAGTTCACGTCAATC-3' 3'-GTCAAGTGCAGTTAG-5' | 3 | +/- |
| Mutant 10 (SEQ ID NOS: 28, 29) | 5'-CAGTTCCCTTCAATC-3' 3'-GTCAAGGGAAGTTAG-5' | 3 | +/- |

*wild-type core sequence of SIF binding element of c-fos promoter: Wagner et al., EMBO J. 9(13):4477-4484 (1990).

Example 2: Preparation of Modified STAT3 Decoys

I. Modifying a STAT3 Decoy for Systemic Administration

The "parent" STAT3 decoy consists of a 15-mer double-stranded oligonucleotide backbone optionally with three phosphorothioate modifications (PTO) at the 3' and 5' end of the double-stranded structure (Leong P L, et al. 2003. p. 4138-43). The PTO modifications do not prevent rapid degradation by enzymes in human plasma and there is no evidence of antitumor efficacy when this formulation is delivered systemically in mice bearing head and neck squamous cell carcinoma (HNSCC) xenografts. To enable systemic administration, the parent STAT3 decoy formulation was modified to: 1) enhance stability and 2) enable uptake into tumors.

The parent decoy, having two complementary oligonucleotide strands, inhibits STAT3-mediated signaling and cancer cell growth when in a duplex formulation. To test the parent decoy, the HNSCC cell line UM-22B was stably transfected with a luciferase gene under the control of high affinity serum inducible element (hSIE) promoter (UM-22B STAT3 Luc 27-11). Cells were plated and after 24 hours, they were transfected with STAT3 decoy (annealed), STAT3 decoy (sense strand), STAT3 decoy (antisense strand) and the respective mutant controls.

The concentration of STAT3 decoy, STAT3 decoy (sense strand) and STAT3 decoy (antisense strand) and their mutant controls used in this assay was based on the $EC_{50}$ (12.6 nM) concentration of the STAT3 decoy in UM-22B cells. Cells were harvested after 24 hours and a luciferase assay was carried out (FIG. 1). These results indicate that the duplex decoy is required to achieve inhibition of STAT3 transcriptional activity.

To stabilize the STAT3 decoy duplex oligonucleotide, a series of chemically modified STAT3 decoys have been designed, synthesized and tested. These modified decoys are being analyzed for their resistance to nucleases and hence stability when administered in vivo. The schematic representations below describe the modified STAT3 decoys tested.

The mutant controls used in the experiments described herein, i.e., "STAT3 mutants" MN4, MS18 and MLNA-1, differ from STAT3 decoys DN4, DS18 and LNA-1 (described below), respectively, by only a single base-pair. For all the STAT3 mutants, the ninth nucleotide in the original STAT3 decoy oligonucleotide sequence has been substituted to T from G.

A. Description of Modified STAT3 Decoys:

The parent and the modified STAT3 decoys consist of a 15-mer oligonucleotide containing both a sense and an antisense strand. In addition, "modified" STAT3 decoys have the following modifications (see Table 2, below).

TABLE 2

Summary of Parent and Modified STAT3 Decoys

| Parent (# 1) and modified (#'s 2-7) STAT3 decoys | Description |
| --- | --- |
| 1. Parent STAT3 decoy | A 15-mer oligonucleotide with 3 phosphorothioate modifications at the 5' and 3' ends of both the strands to act as a blocker of exonuclease activity. |
| 2. DH3S | A 15-mer oligonucleotide with 3 phosphorothioate modifications at the 5' end of one strand and 3' end of the other. The two strands are linked at one end by a hairpin consisting of 3 nucleotides to maintain the double stranded conformation. |
| 3. DH4S | A 15-mer oligonucleotide with 3 phosphorothioate modifications at the 5' end of one strand and 3' end of the other. The two strands are linked at one end by a hairpin consisting of 4 nucleotides. |
| 4. DN4 | A 15-mer oligonucleotide with 3 phosphorothioate modifications at the 5' and 3' end of both the strands. The two strands are linked at one end by a hairpin consisting of 4 nucleotides. |
| 5. DS18 | A 15-mer oligonucleotide with 3 phosphorothioate modifications at the 5' end of the sense strand and the 3'end of the antisense strand. The two strands are linked at one end by a hairpin consisting of 18-atom hexa-ethyleneglycol (C-18) spacers which do not physically interact with any DNA or with any DNA binding enzymes. |
| 6. LNA | A 15-mer oligonucleotide with 3 locked nucleic acid's (LNA) at the 5' end of the sense strand and the 3' end of the antisense strand and two LNA's at the 3'end of the sense strand and the 5'end of the antisense strand. The two strands are linked at one end by C-18 spacer (18-atom hexa-ethyleneglycol). |
| 7. LNA-1 | A 15-mer oligonucleotide with 1 locked nucleic acid (LNA) at the 5' end of one strand and 3' end of the other. The two strands are linked at one end by a hairpin consisting of C-18 spacer (18-atom hexa-ethyleneglycol). |

1. STAT3 Parent Decoy:

Three phosphorothioate modifications at the 5' and 3' ends of both the strands were included to act as a blocker of exonuclease activity. Stat3 Decoy sequence was 5'-CATTTCCCGTAAATC-3' (SEQ ID NO:30), 3'-GTAAAGGGCATTTAG-5' (SEQ ID NO: 5) and the mutant control decoy sequence was 5'-CATTTCCCT-TAAATC-3' (SEQ ID NO: 6), 3'-GTAAAGGGAATTTAG-5' (SEQ ID NO: 7). The first three bases and the last three bases in every sequence are phosphorothioated.

2. Modified Decoys:

For all the modified STAT3 decoys, the original parent STAT3 15-mer oligonucleotide sequence was modified as described below.

In order to maintain the two strands of the parent STAT3 decoy together, initial modifications included either three or four nucleotides in the hairpin, which have been shown to increase the stability of any double-stranded structure (Hirao I, et al. Nucleic acids research 1994; 22(4):576-82; Antao V P, Tinoco I, Jr. Nucleic acids research 1992; 20(4):819-24). Hence the first two modifications (DH3S and DH4S, described below) were designed to include either three (DH3S) or four (DH4S) nucleotides forming a hairpin in the parent STAT3 decoy structure that will maintain the two strands together.

DH3S:

For DH3S, three phosphorothioate modifications were included at the 5' end of one strand and the 3' end of the other strand. The two strands were linked at one end by a hairpin consisting of three nucleotides (GAA) to maintain the double stranded conformation.

Figure 2:
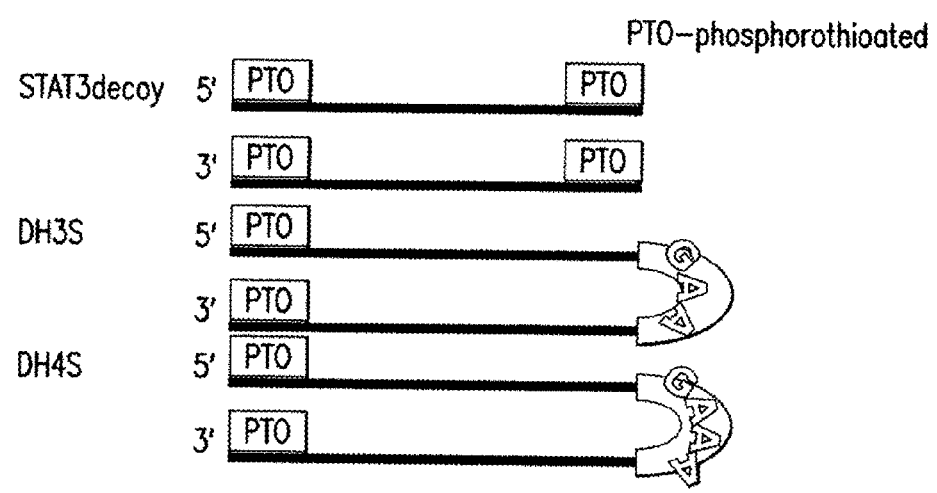
FIG. 2. Depicts a schematic representation of the parent STAT3 decoy, DH3S STAT3 decoy and DH4S STAT3 decoy.

DH4S:

For DH4S, three phosphorothioate modifications were included at the 5' end of one strand and the 3' end of the other strand. The two strands were linked at one end by a hairpin consisting of four nucleotides (GAAA). The parent STAT3 decoy, DH3S and DH4S are illustrated in FIG. 2.

Figure 3:
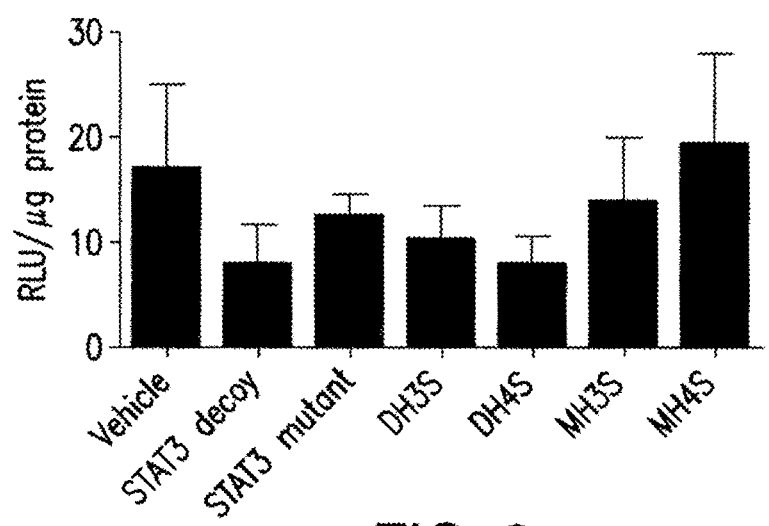
FIG. 3. Depicts the results of a luciferase assay wherein UM-22B cells stably transfected with a luciferase construct under the control of STAT3 hSIE promoter elements were treated with parent STAT3 decoy and modified decoys DH3S and DH4S, and their mutant controls, at a dose of 12.6 nM for 24 hours in the presence of serum containing media. Luciferase assay was done after 24 hours. DH4S demonstrated downmodulation of promoter activity which was comparable to the parent STAT3 decoy.

The DH3S and DH4S decoys were tested for their effects on STAT3 promoter activity and compared to the parent (unmodified) STAT3 decoy. For this assay, the HNSCC stable cell line UM-22B STAT3 Luc 27-11, as described above, was used. Cells were plated and after 24 hours, transfected with STAT3 decoy, DH3S and DH4S and their respective mutant controls. The concentration of STAT3 decoy, DH3S and DH4S used in this assay was based on the $EC_{50}$ (12.6 nM) concentration of the STAT3 decoy in UM-22B cells. Cells were harvested after 24 hours and luciferase assay was carried out (FIG. 3).

Of the two modified decoys, DH3S and DH4S, DH4S demonstrated downmodulation of promoter activity which was comparable to the parent STAT3 decoy.

Figure 4:
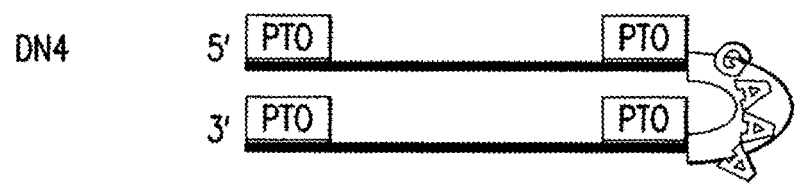
FIG. 4. Depicts a schematic representation of the DN4 STAT3 decoy.

DN4:

In this modification, three phosphorothioate modifications at the 5' end of one strand and 3' end of the other strand and the two strands were linked at one end by a hairpin consisting of four nucleotides (GAAA). DN4 is illustrated in FIG. 4.

DS18:

In order to keep the double-stranded STAT3 decoy oligonucleotide structure together, and simultaneously make the decoy resistant to S1 nuclease, an oligonucleotide with C-18 spacers (an 18-atom hexa-ethyleneglycol molecule) linking the two strands was designed. C-18 spacers are structurally different from the DNA backbone, and do not physically interact with any DNA or with DNA binding enzymes.

Figure 5A:
FIGS. 5A-B. Depicts a schematic representation of the DS18 STAT3 decoy in FIG. 5A and the C-18 spacer in FIG. 5B.
Figure 5B:
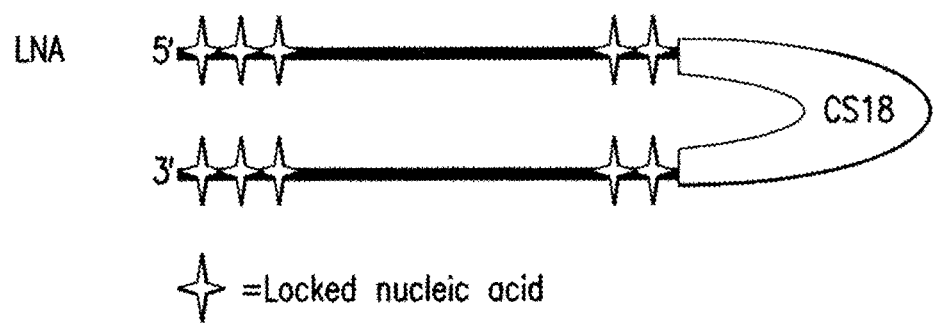

The DS18 modification comprises three phosphorothioate modifications at the 5' end in the sense strand and the 3' end in the antisense strand. The two strands were linked at one end by a hairpin consisting of C-18 spacers. DS18 is illustrated in FIG. 5a and the C-18 spacer is illustrated in FIG. 5b.

Figure 6:
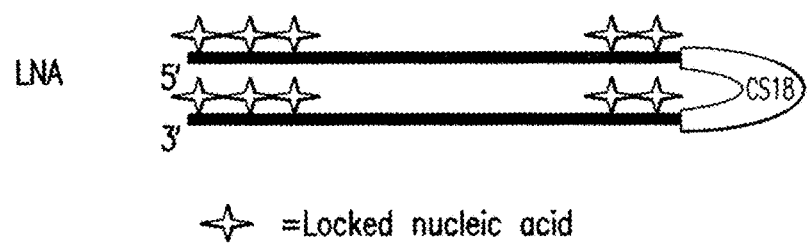
FIG. 6. Depicts a schematic representation of the LNA STAT3 decoy.

LNA:

The use of locked nucleic acid (LNA) in the design of STAT3 decoy to further enhance stability was also evaluated. Three locked nucleic acid's (LNA) were placed at the 5' end of the sense strand and the 3' end of the antisense strand and two LNA's were placed at the 3'end of the sense strand and the 5'end of the antisense strand. The two strands are linked at one end by C-18 spacer (18-atom hexa-ethyleneglycol). LNA is illustrated in FIG. 6.

Figure 7A:
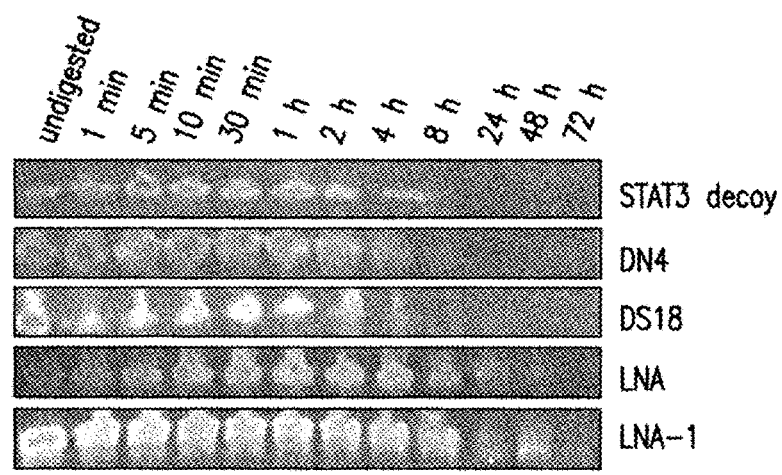
FIGS. 7A-B. Shows the results of a serum stability assay determining the half-life of the parent STAT3 decoy (identified as "STAT3 decoy") and modified STAT3 decoys (e.g., DN4, DS18, LNA, and LNA-1) studied.
Figure 7B:
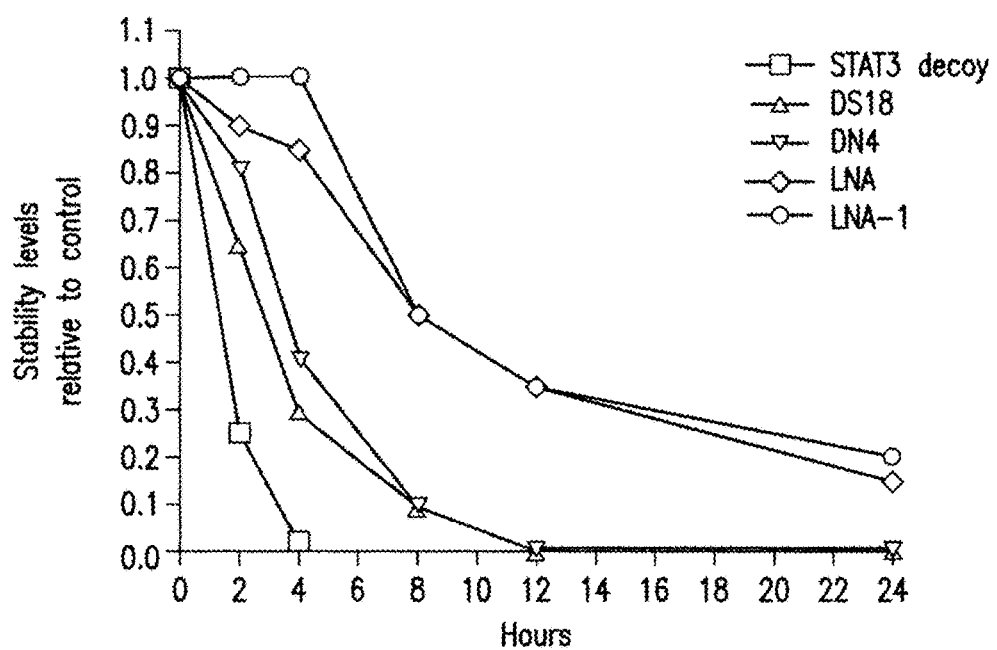

In order to identify a STAT3 decoy molecule that has increased affinity for the target transcription factor and is also stable in biological media, the next series of modified decoys were evaluated for susceptibility to nuclease degradation. The STAT3 parent decoy, DN4, DS18 and LNA were incubated in mouse serum for increasing amounts of time (1 minutes to 72 hours) and then analyzed on a 15% TBE+7 M urea gel to assess degradation. The serum stability assay demonstrated increased resistance of DN4, DS18 and LNA to serum nucleases compared to the parent STAT3 decoy (FIG. 7A-B). LNA is stable up to 8 hours whereas DN4 is stable up to 4 hours, DS18 up to 3.5 hours and the parent STAT3 decoy is resistant up to 1.5 hours.

Figure 8:
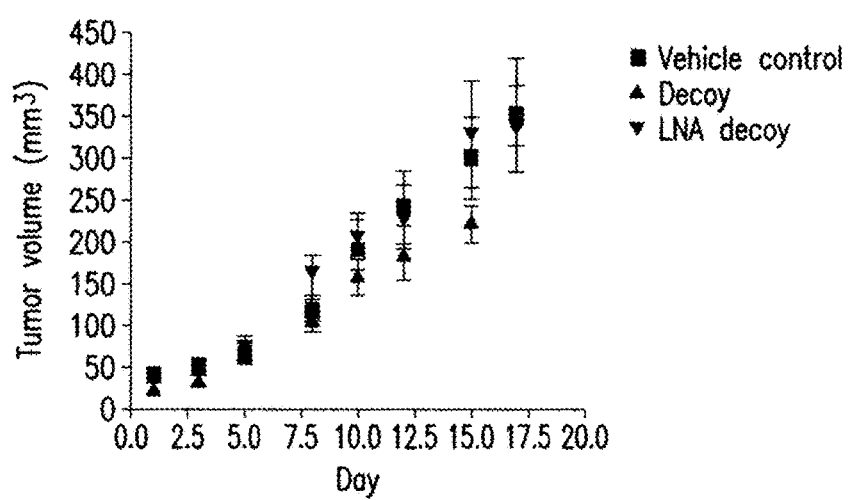
FIG. 8. Illustrates the effect of systemic delivery of parent STAT3 decoy and LNA in HNSCC xenografts. UM-22B cells ($2 \times 10^6$ cells/mouse) were inoculated subcutaneously in 24 athymic nude mice. The same day the mice received daily intravenous injections of saline, parent STAT3 decoy or LNA. Tumors were measured three times per week. At the end of day 17, the xenograft tumors showed no decrease in tumor volume compared to the vehicle control tumors demonstrating no antitumor efficacy of LNA or parent STAT3 decoy administered systemically.

Based on the increased stability of this LNA-modified decoy, an in vivo experiment was performed where the parent STAT3 decoy and the LNA modified decoy were given systemically to test the antitumor efficacy. Athymic nude mice were used for this study and there were 8 mice per group. The treatment groups included: (i) vehicle control (saline), (ii)—STAT3 decoy, and (iii) LNA modified decoy. The xenografts were generated with the head and neck cancer cell line UM-22B. On the same day of tumor cell inoculation, mice were treated with daily intravenous (i.v.) injections of saline, the parent STAT3 decoy or the LNA modified decoy (100 μg STAT3 decoy or LNA modified decoy/mouse/day). During the 17-day treatment period, tumor volumes were measured three times a week. At the end of the treatment period, the mice were sacrificed. As shown in FIG. 8, intravenous administration of the parent or the LNA-modified decoys failed to abrogate tumor growth.

Analyses of the tumor volumes showed no difference between the mice treated with LNA modified decoy and vehicle (saline), suggesting that the LNA modified decoy does not have antitumor efficacy. Also, the tumor volumes in the mice treated with saline as a vehicle control and the parent STAT3 decoy were similar, indicating that the parent STAT3 decoy is degraded by the serum nucleases, thereby supporting the rationale for modifying the STAT3 decoy to enhance stability.

Without intending to be bound by any particular theory, it is possible that these initial attempts to place LNA modifications on the STAT3 decoy were not successful if the LNA moieties interfered with the accessibility of the STAT3 binding region in the LNA to pSTAT3 protein. It has been reported that positioning of internal LNA in an oligonucleotide may interfere with affinity as well as stability (Crinelli R, et al. Nucleic acids research 2004; 32(6):1874-85). Moreover, LNA modification of an oligonucleotide changes the conformation of the neighboring residues from the B-form to the A form (Di Giusto D A, King G C. Nucleic acids research 2004; 32(3):e32).

To test this hypothesis, the binding affinity of the parent STAT3 decoy to tyrosine phosphorylated recombinant STAT3 was determined by surface plasmon resonance (SPR). Solutions of STAT3 decoy were prepared at multiple concentrations and passed over STAT3 immobilized in a sensor chip and measured on a BIAcore 3000 instrument and affinities calculated by the BIAevaluation software (Version 4.1, BIAcore). The amount of STAT3 decoy bound to STAT3 increased directly with increasing concentrations of STAT3 decoy in the test solutions. Data analysis by fitting the sensorgrams to a Langmuir 1:1 model of binding yielded kinetic and affinity values (Table 3).

TABLE 3

The affinities of Stat3 decoy to Stat3 calculated from Langmuir binding analysis.

| Conc of Stat3 decoy | $k_a$ (1/Ms) | $k_d$ (1/s) | $K_A$ (1/M) | $K_D$ (M) | Chi$^2$ |
|---|---|---|---|---|---|
| 5 mM | $2.68 \times 10^4$ | $4.84 \times 10^{-3}$ | $5.52 \times 10^6$ | $1.81 \times 10^{-7}$ | 0.287 |
| 10 mM | $2.21 \times 10^4$ | $2.85 \times 10^{-3}$ | $7.75 \times 10^6$ | $1.29 \times 10^{-7}$ | |
| 20 mM | $9.34 \times 10^3$ | $5.17 \times 10^{-3}$ | $1.81 \times 10^6$ | $5.54 \times 10^{-7}$ | |
| 40 mM | $5.71 \times 10^3$ | $3.77 \times 10^{-3}$ | $1.52 \times 10^6$ | $6.59 \times 10^{-7}$ | |
| 80 mM | $5.25 \times 10^3$ | $5.2 \times 10^{-3}$ | $1.01 \times 10^6$ | $9.91 \times 10^{-7}$ | |

In contrast to the parent STAT3 decoy, the decoy modified with 10 LNA molecules did not bind to STAT3.

LNA-1:

In order to eliminate the effect of conformational change in the actual binding region, the parent the STAT3 decoy was modified with only one LNA at the 5' and 3' ends of the two strands to increase stability as well as efficacy.

Figure 9:
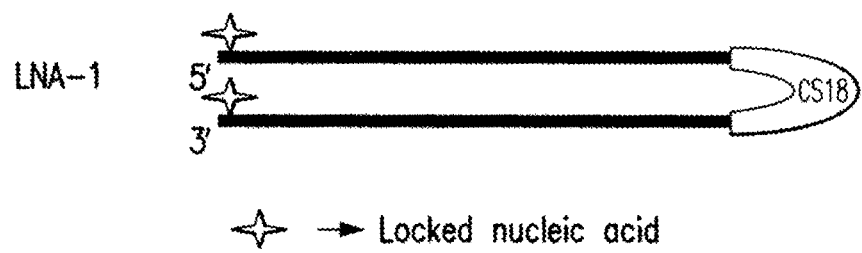
FIG. 9. Depicts a schematic representation of the LNA-1 STAT3 decoy.

LNA-1 contains one locked nucleic acid (LNA) at the 5' end of one strand and 3' end of the other strand. The two strands are linked at one end by a hairpin consisting of C-18 spacer. LNA-1 is illustrated in FIG. 9.

As described above with respect to LNA, the stability of LNA-1 in serum nucleases where LNA-1 was exposed to serum for increasing amounts of time (1 minute to 72 hours) was tested and then analyzed on a 15% TBE+7 M urea gel to assess degradation. The serum stability assay demonstrated a half-life of LNA-1 up to at least 8 hours compared to 1.5 hours for STAT3 decoy (see FIG. 7A-B).

Figure 10:
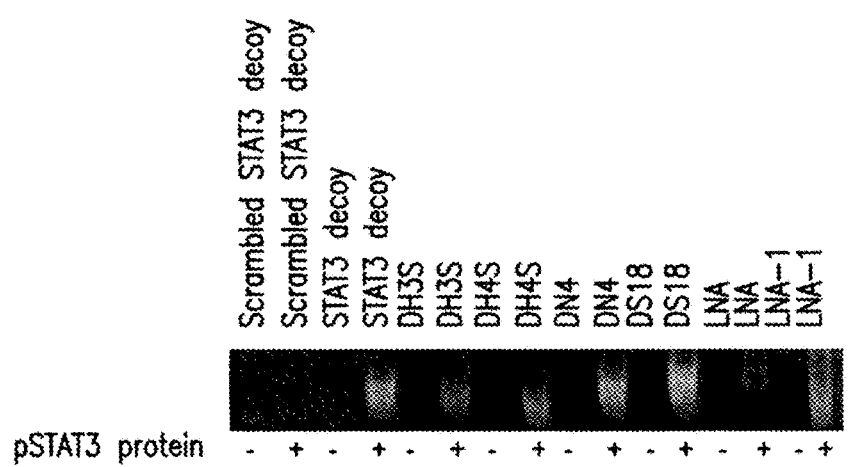
FIG. 10. Depicts the binding of parent STAT3 decoy and the modified STAT3 decoys to pSTAT3 protein, which were evaluated by gel electrophoresis using a sensitive fluorescent stain to detect double or single-stranded DNA. The parent STAT3 decoy and the modified decoys were incubated with pSTAT3 protein and ran on a 6% polyacrylamide-TBE gel. The gel was stained with SYBR Gold Nucleic Acid stain and subjected to transillumination and photographed using Polaroid 667 black and white print film.

II. Binding of STAT3 Decoy and Modified STAT3 Decoys to pSTAT3 Protein:

The binding of STAT3 decoy and the modified STAT3 decoys to pSTAT3 protein were evaluated by gel electrophoresis using a sensitive fluorescent stain to detect double or single-stranded DNA (FIG. 10). As shown in FIG. 10, the DN4, DS18 and LNA-1 modified decoy bound to recombinant pSTAT3 protein as well as the parent decoy and with greater apparent avidity than the other modified decoys tested.

To more quantitatively assess the affinity of the decoy for pSTAT3 protein, the binding affinity by surface plasmon resonance (SPR) was determined. Solutions of STAT3 decoy were prepared at multiple concentrations and passed over recombinant tyrosine phosphorylated STAT3 immobilized in a sensor chip.

The amount of parent STAT3 decoy and modified STAT3 decoys bound to recombinant pSTAT3 increased directly with increasing concentrations of STAT3 decoy in test solutions. Data analysis by fitting the sensorgrams to a Langmuir 1:1 model of binding yielded kinetic and affinity values (Table 4).

TABLE 4

The affinities of parent STAT3 decoy and modified STAT3 decoys to STAT3 calculated from Langmuir binding analysis

| Decoys | $k_a$ (1/Ms) | $k_d$ (1/s) | $K_A$ (1/M) | $K_D$ (M) | Chi$^2$ |
|---|---|---|---|---|---|
| STAT3 decoy | $5.85 \times 10^4$ | $7.16 \times 10^{-3}$ | $5.50 \times 10^6$ | $1.22 \times 10^{-7}$ | 0.704 |
| DN4 | $4.14 \times 10^4$ | $7.53 \times 10^{-3}$ | $5.50 \times 10^6$ | $1.82 \times 10^{-7}$ | 1.26 |
| DS18 | $4.76 \times 10^4$ | $6.79 \times 10^{-3}$ | $7.02 \times 10^6$ | $1.42 \times 10^{-7}$ | 1.26 |

The surface plasmon resonance (SPR) data confirms the binding of the unmodified STAT3 decoy, DN4, and DS18 to pSTAT3 protein.

Figure 11:
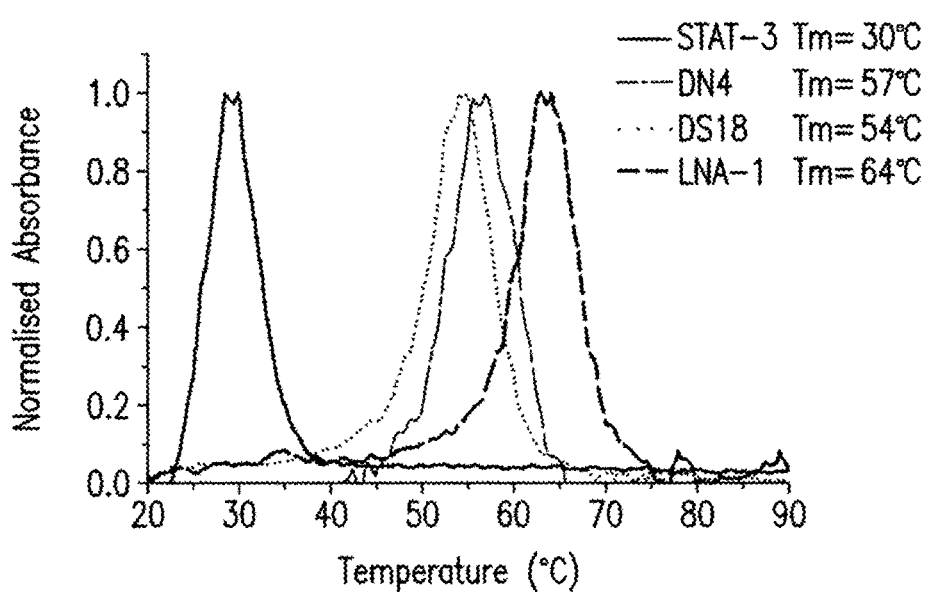
FIG. 11. Thermal denaturation of various STAT3 decoys such as parent STAT3, DN4, DS18 and LNA-1 were monitored at 260 nm at the heating and cooling rate of 1° C./min from 20° C. to 90° C. The melting transitions were determined from the first derivatives of the UV-melting curves.

Next, the melting temperature for the parent STAT3 decoy, DN4, DS18 and LNA-1 decoys were assessed to evaluate their thermal stability. Melting temperature was determined using a Varian Cary 300 Bio spectrophotometer equipped with a thermoelectrically controlled multicell holder, using 1.5 µM strand concentration each in 10 mM Tris and 1 mM EDTA, pH 8.0. The parent (unmodified) and modified decoys were subjected to thermal denaturation at 260 nm at the heating and cooling rate of 1° C./min from 20 to 90° C. from which the melting temperature was determined. Melting transitions (Tm values) were determined by taking the first derivatives of the UV-melting curves (see FIG. 11).

Figure 12A:
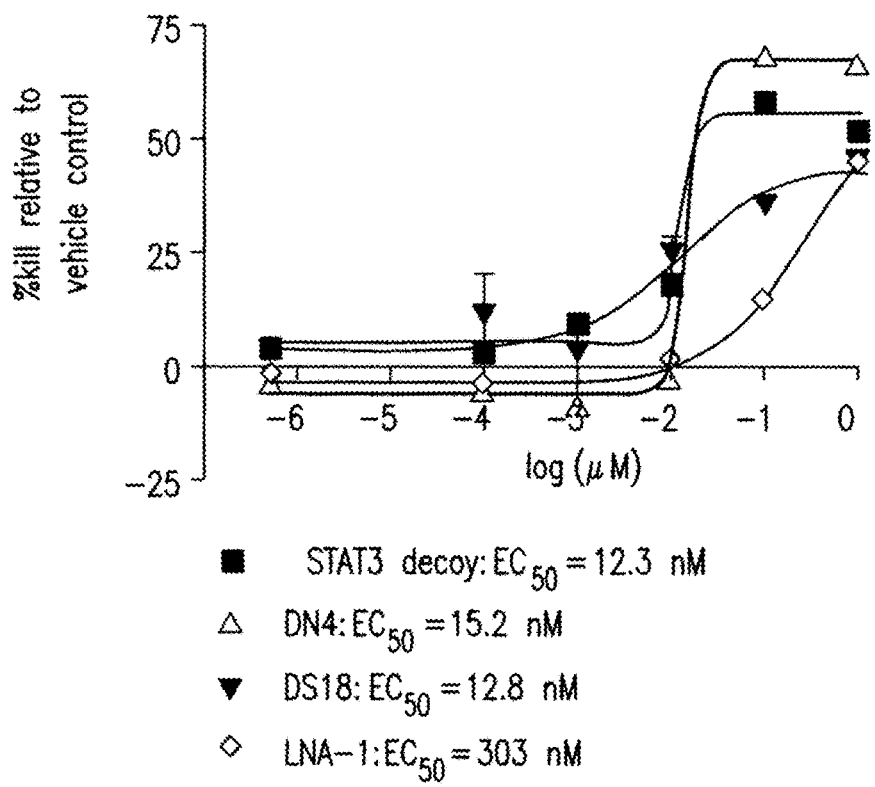
FIGS. 12A-B. Depicts dose response curves of FIG. 12A parent STAT3 decoy, DN4, DS18 and LNA-1 and FIG. 12B parent STAT3 decoy, DN4, DS18 in an HNSCC cell line. Cells were exposed to varying concentrations of parent STAT3 decoy, DN4, DS18 and LNA-1 in presence of lipofectamine (LPA) 2000. MTT assay was done after 72 hours to determine cell viability from which % kill was determined. Control wells contained saline in presence of LPA 2000. For each data point, n=3. For (FIG. 12A), 1483 cells were used. In (FIG. 12B), UM-SCC1 cells were used.

The melting temperature demonstrated increased thermal stability for all of the modified decoys tested as compared to the parent STAT3 decoy. To verify that these stabilized decoys maintained their biologic activity in HNSCC cells, their impact on growth was examined. Cells (30,000 cells/well) were seeded in a 24-well plate in DMEM containing FBS. After 24 hours, cells were transfected with varying concentrations from 1 µM-0.0001 µM of the STAT3 decoy, DN4 and DS18 in presence of OPTIMEM and lipofectamine 2000. After 4 hours, the transfection media was replaced with DMEM containing 10% serum. At the end of 72 hours, MTT assay was performed to determine the EC50 concentration It was found that the modified STAT3 decoys tested (DN4, DS18, LNA-1) inhibited head and neck cancer cell proliferation in vitro at nanomolar concentrations with $EC_{50}$ ranging from 12.3 nM for STAT3 decoy, 15.3 nM for DN4, 12.8 nM for DS and 303 nM for LNA-1 in 1483 cells (FIG. 12A).

Figure 12B:
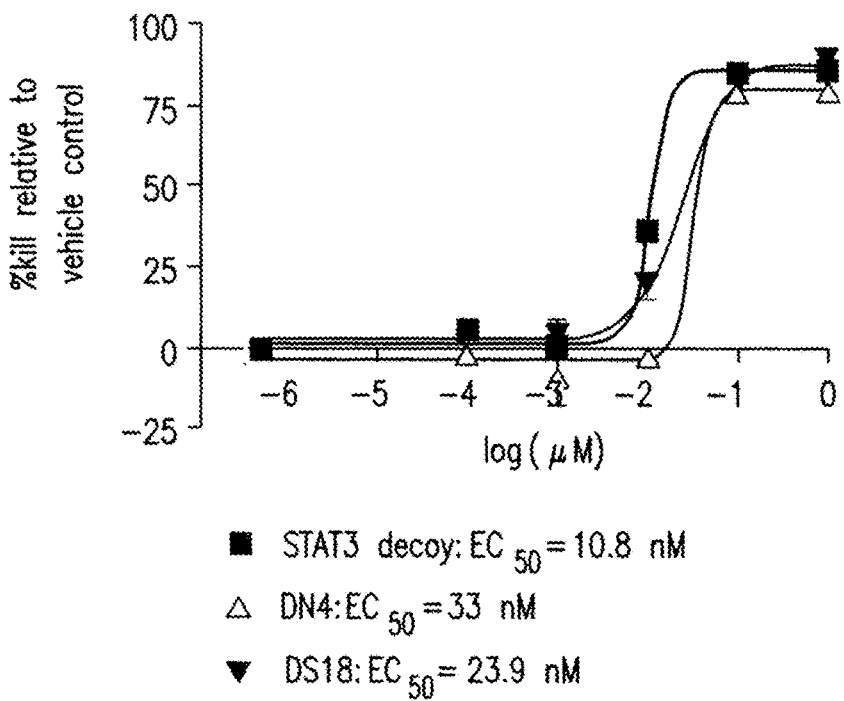

In a second experiment, UM-SCC1 cells were used. UM-SCC1 cells (30,000 cells/well) were seeded in a 24-well plate in DMEM containing FBS. After 24 hours, cells were transfected with varying concentrations from 1 µM-0.0001 µM of the STAT3 decoy, DN4 and DS18 in presence of OPTIMEM and lipofectamine 2000. After 4 hours, the transfection media was replaced with DMEM containing 10% FBS. At the end of 72 hours, MTT assay was performed to determine the $EC_{50}$ concentration (FIG. 12B).

Figure 13A:
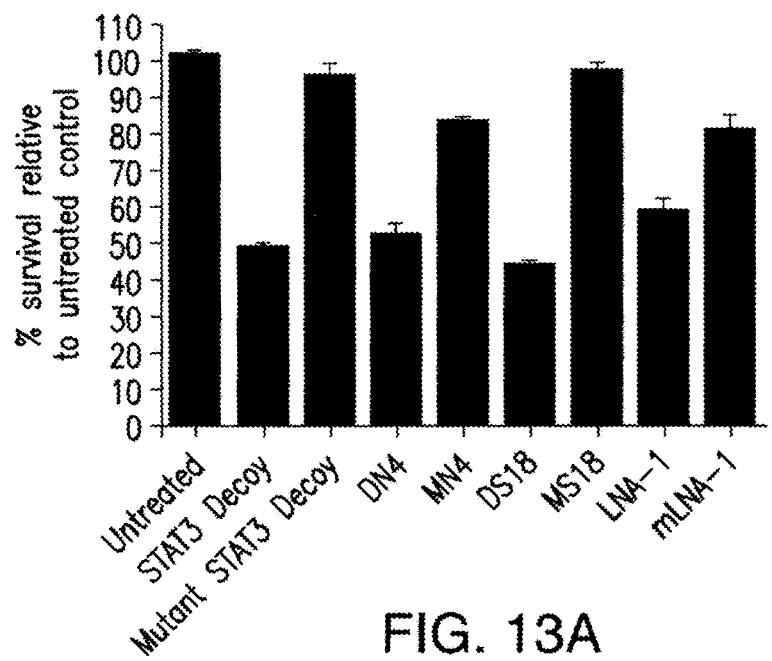
FIGS. 13A-B. Illustrates that modified STAT3 decoys (DN4, DS18, LNA-1) decrease cell viability similar to the parent STAT3 decoy in HNSCC cells. 1483 cells were transfected with STAT3 decoy/mutant, DN4/MN4, DS18/MS18, and LNA-1/mLNA-1 in FIG. 13A and UM-SCC1 cells transfected with STAT3 decoy/mutant, DN4/MN4 and DS18/MS18 in FIG. 13B) at their $EC_{50}$ concentrations for 4 hours and replaced with DMEM+10% FBS. After 72 hours, cell viability was determined by MTT assay. Results in A are from 3 separate experiments.
Figure 13B:
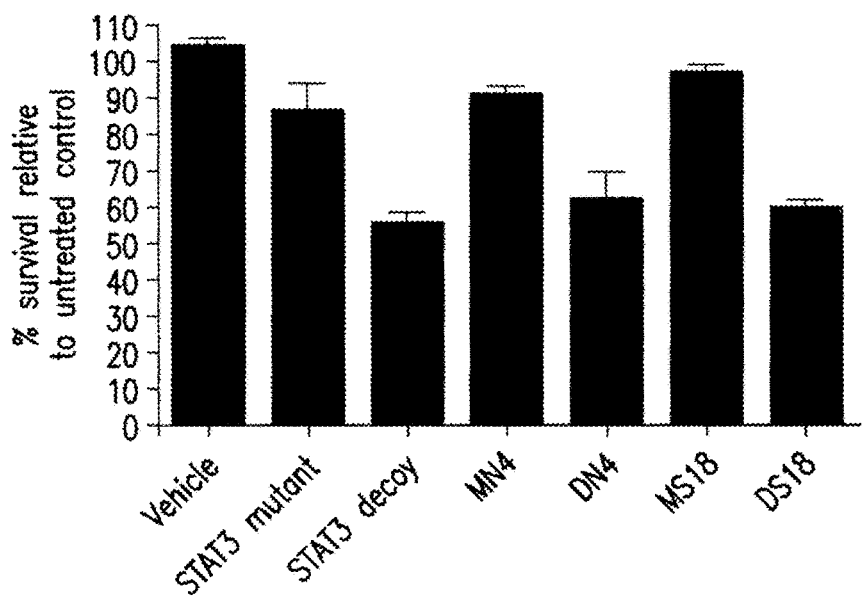

In an assay measuring percent survival rate of cells transfected with STAT3 decoys, it was found that modified STAT3 decoys decreased cell viability similar to the parent STAT3 decoy in HNSCC cells. 1483 cells (30000 cells/well) were plated in a 24 well plate and after 24 hours transfected with the parent STAT3 decoy or the modified decoys and their respective mutant controls. The mutant decoys differ from the parental STAT3 decoy by only a single base-pair. The cells were transfected with STAT3 decoy, DN4, DS18 and LNA-1 and their respective mutant controls (MN4, MS18, and MLNA-1) at the $EC_{50}$. Results from this experiment demonstrated that the modified decoys resulted in about 50% decrease in cell survival which was comparable to the parent STAT3 decoy (FIG. 13A). The data are represented as SEM of triplicate samples. These results are from three separate experiments. Results from a second experiment in UM-SCC1 cells for DN4/MN4 and DS18/MS18 are set forth in FIG. 13B. These results indicate that the modified STAT3 decoys kill the cells. In contract, cells treated with the mutant control modified decoys are not toxic.

Of the STAT3 modified decoys tested, three (DN4, DS18 and LNA-1) have been shown to bind to pSTAT3 as well as the parent STAT3 decoy. These three modified decoys have also shown increased half-life (about 4 hours for DN4, about 3.5 hours for DS18 and almost 8 hours for LNA-1) compared to the parent STAT3 decoy which is only stable up to about 1.5 hours. Despite increased stability, the modified decoys have not demonstrated enhanced inhibition of HNSCC growth in vitro that is increased as compared to the parent decoy as indicated by $EC_{50}$ values, although all three do inhibit cancer cell proliferation in vitro.

III. Design of Cyclic STAT3 Decoys

The STAT3 decoy duplex oligonucleotide will be circularized to increase binding affinity and resistance to serum nucleases.

Figure 14:
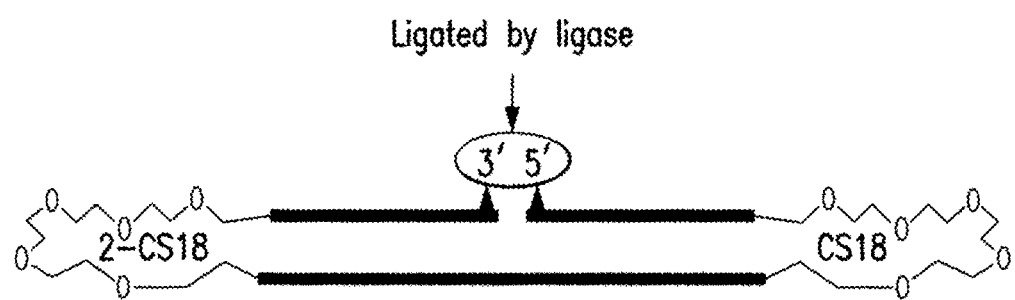
FIG. 14. Depicts a schematic representation of the 2-CS18 STAT3 decoy.

2-CS18 STAT3 Decoy:

The cyclic STAT3 decoy will consist of a 15-mer double stranded oligonucleotide where the two strands are linked by C-18 spacers at two ends. The circular oligonucleotide is constructed by circularization of the 3' and 5' ends of the oligonucleotides by enzymatic ligation. Since enzymatic degradation generally occurs from the 3' end of single strands and frayed ends of duplexes, cyclization of the two strands will confer greater resistance against nucleases. The 2-CS18 STAT3 decoy is illustrated in FIG. 14.

Figure 15A:
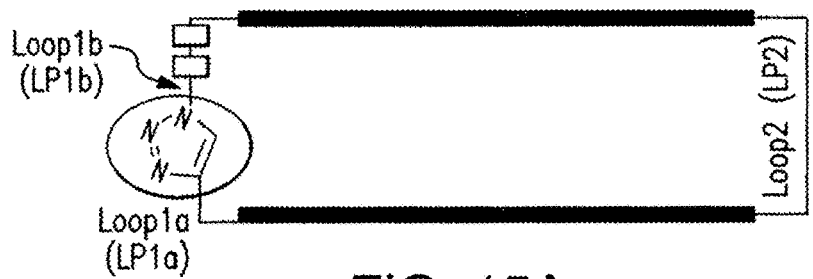
FIGS. 15A-B. Depicts a schematic representation of the 2 LP STAT3 decoy (FIG. 15A) and LP1a, LP2, and LP1b (FIG. 15B).
Figure 15B:
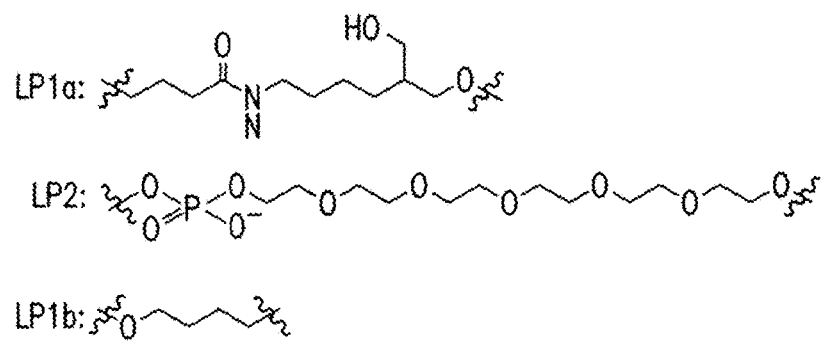

2 LP-STAT3 Decoy:

This modification will have the parent STAT3 decoy backbone (without PTO modifications) and the 5' end of the sense and the 3' end of the antisense linked through LP1a (LP1a) and LP1b (LP1b) spacers where as the 3' end of the sense and the 5' end of the antisense are linked by LP2. The 2 LP-STAT3 decoy is illustrated in FIG. 15A. LP1a, LP2, and LP1b are illustrated in FIG. 15B.

This design differs from 2-CS18 STAT3 (described above) in that it utilizes an optimized set of spacers recently developed by El-Sagheer et al. (Chembiochem 2008; 9(1): 50-2)) that show unusually high enzymatic and thermodynamic stabilities.

The cyclic oligonucleotides will maintain the B-form conformation and are expected to demonstrate increased thermodynamic stability arising from the intramolecular nature of the construct. The cyclic STAT3 decoys are expected to remain double-stranded in the cell, exhibit high resistance to nucleases and will be more easily internalized by the cells than their acyclic counterpart.

Maximum efficacy of a systemically delivered STAT3 decoy to the target tumor site requires uptake by the tumor cells. One approach to enhance uptake is to covalently attach polyunsaturated fatty acids (PUFAs) to the cyclic STAT3 decoy. This strategy is utilized to deliver the modified STAT3 decoy with the greatest stability to enhance uptake into the HNSCC tumor when administered systemically.

Figure 16A:
FIGS. 16A-B. Depicts a schematic representation of the 2 LP DHA STAT3 decoy (FIG. 16A) and LP1a, LP1b, T1, and DHA (FIG. 16B).
Figure 16B:
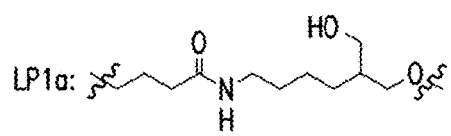
Figure 16B:
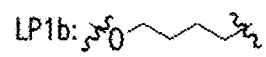
Figure 16B:
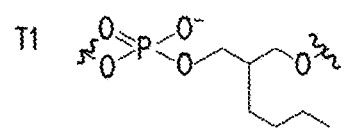
Figure 16B:
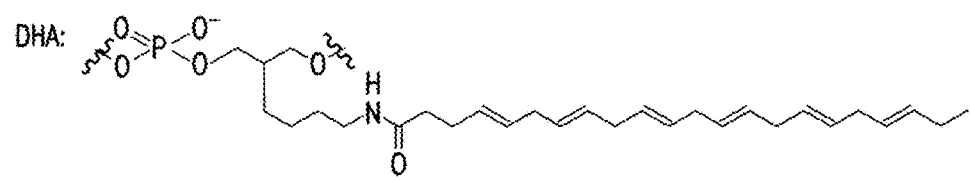

2 LP DHA-STAT3 decoy: This modification will have the parent STAT3 decoy backbone (without PTO modifications) and the 5' end of the sense and the 3' end of the antisense are linked by LP1a-Monomer (LP1a-M) and the LP1b-Monomer (LP1b-M) where as the 3' end of the sense and the 5' end of the antisense are linked by T1 with DHA attached to it. The 2 LP DHA-STAT3 decoy is illustrated in FIG. 16A. LP1a, LP1b, T1, and DHA are illustrated in FIG. 16B.

Figure 17:
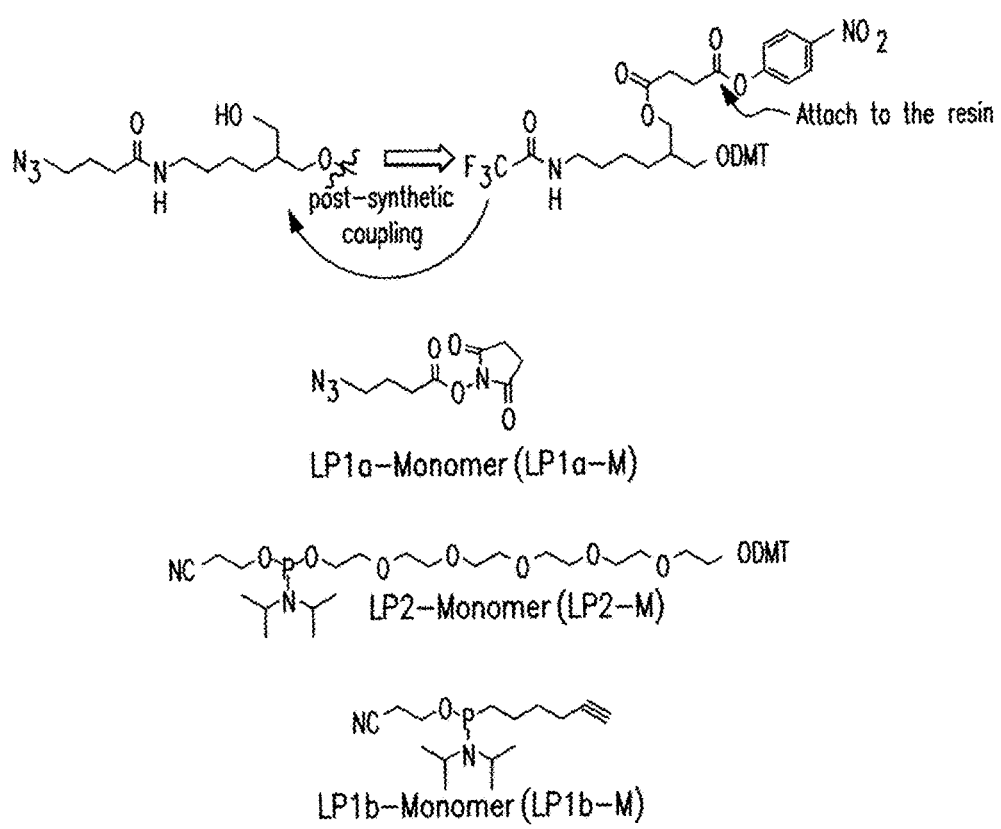
FIG. 17. Depicts the LP1a-Monomer (LP1a-M), the LP1b-Monomer (LP1b-M), and the LP2-Monomer (LP2-M).

Methods for preparing some of these units individually have been established (El-Sagheer A H, et al. Chembiochem 2008; 9(1):50-2; Kocalka P, et al. Chembiochem 2008; 9(8):1280-5). The LP1a-Monomer (LP1a-M), the LP1b-Monomer (LP1b-M), and the LP2-Monomer (LP2-M) are illustrated in FIG. 17.

These further STAT3 decoys will systematically be tested for their binding affinity to pSTAT3 protein, nuclease degradation and efficacy in HNSCC preclinical models.

Example 3: Summary of Surface Plasmon Resonance (SPR) Analysis for pSTAT3: Binding of Decoy and Modified Decoys I. Materials and Methods Solution Preparation All the buffers and ddH$_2$O were degassed and filtered (0.22 um filter) before use in all the SPR experiments.

Instrument Preparation

A cleaning step utilizing the Desorb protocol was performed with reagents supplied by BIAcore (0.5% SDS and 50 mM glycine at pH 9.5). This was followed by a second step of Superclean with freshly prepared solutions (1% HAc, 0.2 M NaHCO$_3$, 6M guanidine-HCl and 10 mM HCL). Once the clean steps were completed, the machine was primed three times with ddH$_2$O. A system test was performed to check the signal quality and the results were compared to previous cleaning protocols to ascertain instrumental performance.

II. Immobilization of pStat3 on a CM5 Chip

Figure 18A:
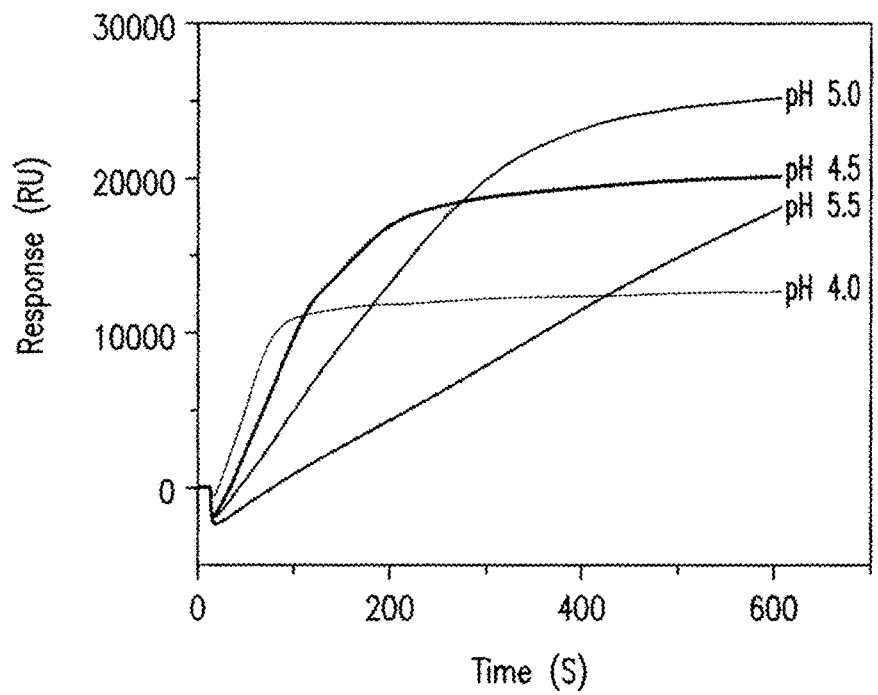
FIGS. 18A-B. Depicts (A): The pH scouting results on pStat3 (20 μg/mL) in 10 mM acetate buffers with different pH; (B) the immobilization process of pStat3 (20 μg/mL) in acetate buffer (pH 5.0) on the CM5 chip. Preliminary pH scouting experiments were performed prior to immobilization of pStat3 on the CM5 chip to determine the optimal pH for pre concentration of ligand (e.g. pStat3) onto CM5 surface (FIG. 18A). The optimized conditions for immobilization of pStat3 were determined using a concentration of pStat3 at 20 μg/mL with acetate buffer at pH 5.0. High capacity surfaces were generated via standard EDC/NHS-mediated amine coupling procedure (FIG. 18B).
Figure 18B:
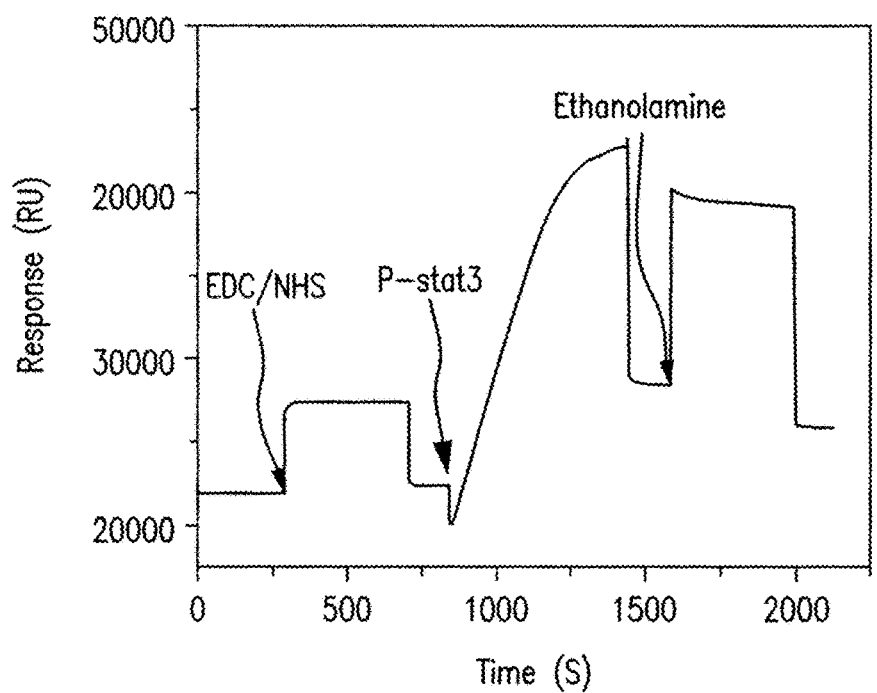

To optimize the activity and stability of pSTAT3, all the experiments were performed at 4° C. including maintaining the sample holders in the Biacore3000 at this temperature with circulating water-bath. Preliminary pH scouting experiments were performed prior to immobilization of pSTAT3 on the CM5 chip to determine the optimal pH for pre-concentration of ligand (e.g., pSTAT3) onto CM5 surface (FIG. 18A). The optimized conditions for immobilization of pSTAT3 were determined using a concentration of pSTAT3 at 20 µg/mL with acetate buffer at pH 5.0. High capacity surfaces were generated via standard EDC/NHS-mediated amine coupling procedure (FIG. 18B). Briefly, a freshly prepared aqueous solution containing 0.2 M EDC and 0.05 M NHS was injected for 7 minutes to activate the CM5 chip, followed by injection of pSTAT3 at 20 µg/mL in acetate buffer (pH 5.0) for 10 minutes. The concentration and duration of STAT3 injection was calculated to obtain signals within a desired RU range. Following STAT3 immobilization, the surface was capped to prevent further reaction by a 7-minute pulse of 1M ethanolamine at pH 8.5, capping excess activated ester groups on the CM5 surface. The average immobilization level of pSTAT3 was about 3825±42 RU determined from two replicated sets of experiments.

III. Binding of Decoy/Modified Decoy to pStat3

All samples of the decoy and modified decoy such as STAT3 decoy, DN4, DS18 and LNA were diluted into running buffer (20 mM HEPES, pH 7.0, 200 mM NaCl, 10 mM MgCl$_2$) with the concentrations across the range of 0.323 µM to ~10 µM except for LNA where the concentration ranged from 5 µM~80 µM. The kinetics measurements were performed by flowing the decoy (or modified decoy) through the reference channel and pSTAT3 affixed channel, at a flow rate of 30 µL/min for 1 minute. At the end of the association phase, the flow rate was maintained to monitor dissociation kinetics for a duration of 3 minutes. A 2M NaCl solution was used as regeneration buffer. Data analysis was performed with the BIAevaluation software. Data were fitted to a 1:1 binding model using global settings for $k_a$ and $k_d$ and modeling various baseline changes (drifts).

The binding results from two replicate experiments determining binding of decoy to different concentrations (0.313 µM, 0.625 µM, 1.25 µM, 2.5 µM, 5.0 µM, 10.0 µM and 0.625 µM, 1.25 µM, 2.5 µM, 5.0 µM, 10.0 µM, 20.0 µM) to pStat3 immobilized on the CM5 chip and their affinities were calculated using above statistical modeling analysis based on the resulting sensorgrams (Table 5A).

TABLE 5A

The affinities of parent decoy to pSTAT3.

| Results | $k_a$ (1/Ms) | $k_d$ (1/s) | $K_A$ (1/M) | $K_D$ (M) | Chi$^2$ |
|---|---|---|---|---|---|
| Experiment 1 | 5.85 × 10$^4$ | 7.16 × 10$^{-3}$ | 8.17 × 10$^6$ | 1.22 × 10$^{-7}$ | 0.704 |
| Experiment 2 | 6.48 × 10$^4$ | 7.46 × 10$^{-3}$ | 8.68 × 10$^6$ | 1.15 × 10$^{-7}$ | 2.2 |
| Mean ± SD | 6.17 ± 0.45 × 10$^4$ | 7.31 ± 0.21 × 10$^{-3}$ | 8.43 ± 0.36 × 10$^6$ | 1.19 ± 0.05 × 10$^{-3}$ | |

The binding of decoy to different concentrations (5 µM, 10 µM, 20 µM, 40 µM, and 80 µM) to pStat3 immobilized on the CM5 chip was repeated again and their affinities were calculated (Table 5B) based on the resulting sensorgrams.

TABLE 5B

The affinities of parent decoy to pSTAT3.

| Results | $k_a$ (1/Ms) | $k_d$ (1/s) | $K_A$ (1/M) | $K_D$ (M) | Chi$^2$ |
|---|---|---|---|---|---|
| Experiment 1 | $2.33 \times 10^4$ | $7.46 \times 10^{-3}$ | $3.12 \times 10^7$ | $3.20 \times 10^{-7}$ | 0.161 |

IV. Stability of pSTAT3 Immobilized on the CM5 Chip

Although all the experiments (immobilization and all binding experiments described in Example 2 and Table 5A and B) were performed at 4° C., the stability of pStat3 may be limited, possibly by loss of phosphorylation with time. Without wishing to be bound by any particular theory, this may explain the decreasing responses observed within the duration of the experiments. Initial responses for the binding of 10 μM decoy to freshly immobilized pStat3 were ~133-136 RU. The responses decreased to 7.7 RU and 7.4 RU, respectively, in the first and second experiments, respectively. It was also observed that the activity of the pStat3 decreased rapidly even within the same day, after freshly immobilizing pStat3 on a new CM5 chip. During attempts to replicate the earlier binding studies of the second experiment, after one complete cycle of kinetic measurements were conducted on the parent decoy and modified decoy, found that the RU decreased significantly after ~4 hours.

The standard deviations for binding of parent decoy to pStat3 were all low since care was taken to measure all the binding interactions of decoy to pStat3 immediately after pStat3 was immobilized on the chip. These were followed sequentially with the binding experiments for the modified decoys, DS18 or DN4. The binding results of the parent (unmodified decoy) were used to ascertain the activity/stability of pStat3, serving as a reference for this purpose. Due to the presumed limited stability of pStat3, the standard deviations for the analysis of modified decoys to pStat3 (DS18 and DN4) are higher than for the unmodified decoy for these reasons.

Example 4: Incorporation of STAT3 Decoys in Microbubbles

Figure 19:
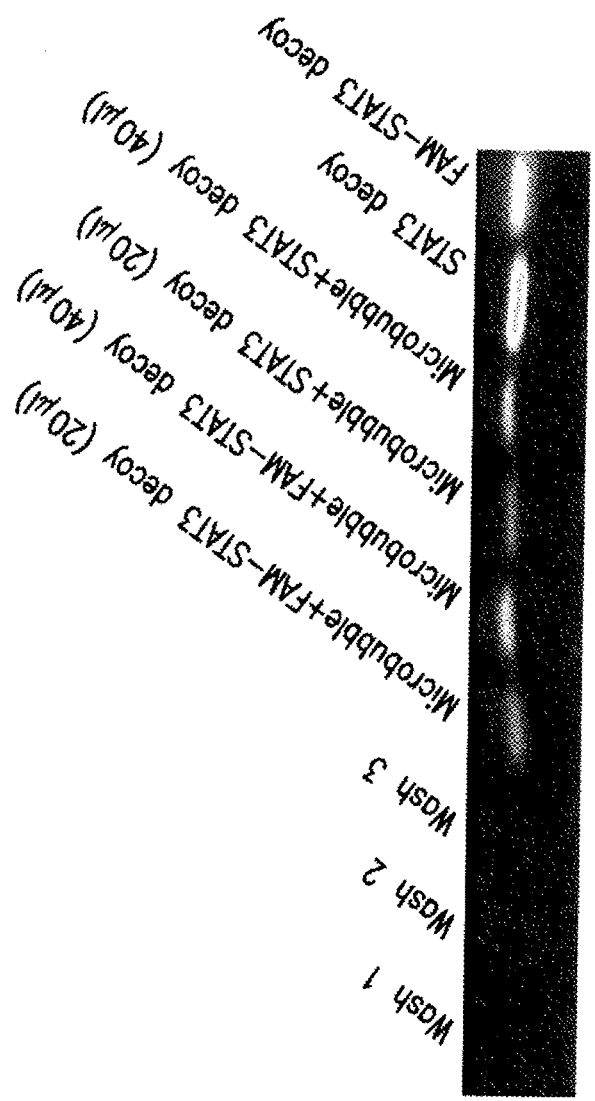
FIG. 19. Depicts the results of incorporation of STAT3 decoy in microbubbles.

Microbubbles were incubated with STAT3 decoy and/or FAM labelled STAT3 decoy and washed several times with 1×PBS. The fluorescence label FAM was connected to the 5' end of the STAT3 decoy oligonucleotide. The STAT3 decoy or FAM-labeled STAT3 decoy was mixed with microbubbles and washed with PBS to remove the unbound STAT3 decoy or microbubbles. The mixture was centrifuged and the wash step was repeated several times. Finally the washes and disrupted microbubbles containing STAT3 decoy or FAM-labeled STAT3 decoy were run on a 6% Polyacrylamide-TBE gel and stained with SYBR Gold Nucleic Acid stain. STAT3 decoy and FAM-STAT3 decoy were used as controls. Results are shown in FIG. 19.

Example 5: Administration of Modified STAT3 Decoy in an In Vivo Animal Model

The modified STAT3 decoys are tested in xenograft studies by inoculating SCCHN tumor cells (1-2×10$^6$) subcutaneously. Once the mice develop palpable tumor nodules (generally 7-14 days later), they are randomized to receive: 1) systemic (intravenous) administration of the modified STAT3 decoy; 2) systemic administration of the mutant control decoy modified similarly to the STAT3 decoy; 3) intratumoral administration of the unmodified STAT3 decoy; or 4) intratumoral administration of the unmodified control decoy. Randomization is carried out using a statistical program based on tumor volumes to assure that mice in each group have a comparable tumor burden. Daily treatments are administered over a range of doses (0-10 mg/kg/daily). The systemic treatments are given by tail vein injection. In all experiments, the mutant control decoy are administered by a similar route as a negative DNA control. Intratumoral administration of the unmodified decoy will be used as a positive control.

Several SCCHN cell lines known to grow well as xenografts in vivo (e.g., 1483, UM-22B, Cal-33) are used. The effect of systemic administration of the modified STAT3 decoy on tumor volumes is examined using subcutaneous xenograft models and the effects on metastasis is tested using the orthotopic xenograft model, wherein SCCHN cells are injected into the floor-of-the-mouth with a high incidence of metastasis to the cervical lymph nodes.

If anti-tumor effects with systemic administration of a modified STAT3 decoy in SCCHN xenograft models are observed, the experiment is repeated in three SCCHN models of EGFR inhibitor resistance. These models include: (1) isogenic SCCHN cells that are resistant to EGFR TKI (erlotinib or gefitinib) in vitro and in vivo and which also demonstrate resistance to cetuximab in vivo; (2) isogenic cells from several SCCHN cell lines that demonstrate resistance to EGFR mAb (cetuximab) in vivo; and (3) isogenic SCCHN cells engineered to express the EGFR mutation EGFRvIII, which lacked an external ligand binding domain thus rendering cells that expressed this altered receptor relatively resistant to cetuximab. All three models of EGFR inhibitor resistance demonstrate increased expression of pSTAT3 and remain sensitive to the growth inhibitory effects of the STAT3 decoy.

The anti-tumor effects of the systemically administered modified STAT3 decoy(s) is examined alone, and in combination with EGFR targeting agents including cetuximab or erlotinib. Isogenic parental (or vector-transfected control) cell lines are used to generate xenografts and used as controls.

Example 6: STAT3 Binding Assay for pStat3 Decoy and Modified Decoys DN4 and DS18

Figure 20:
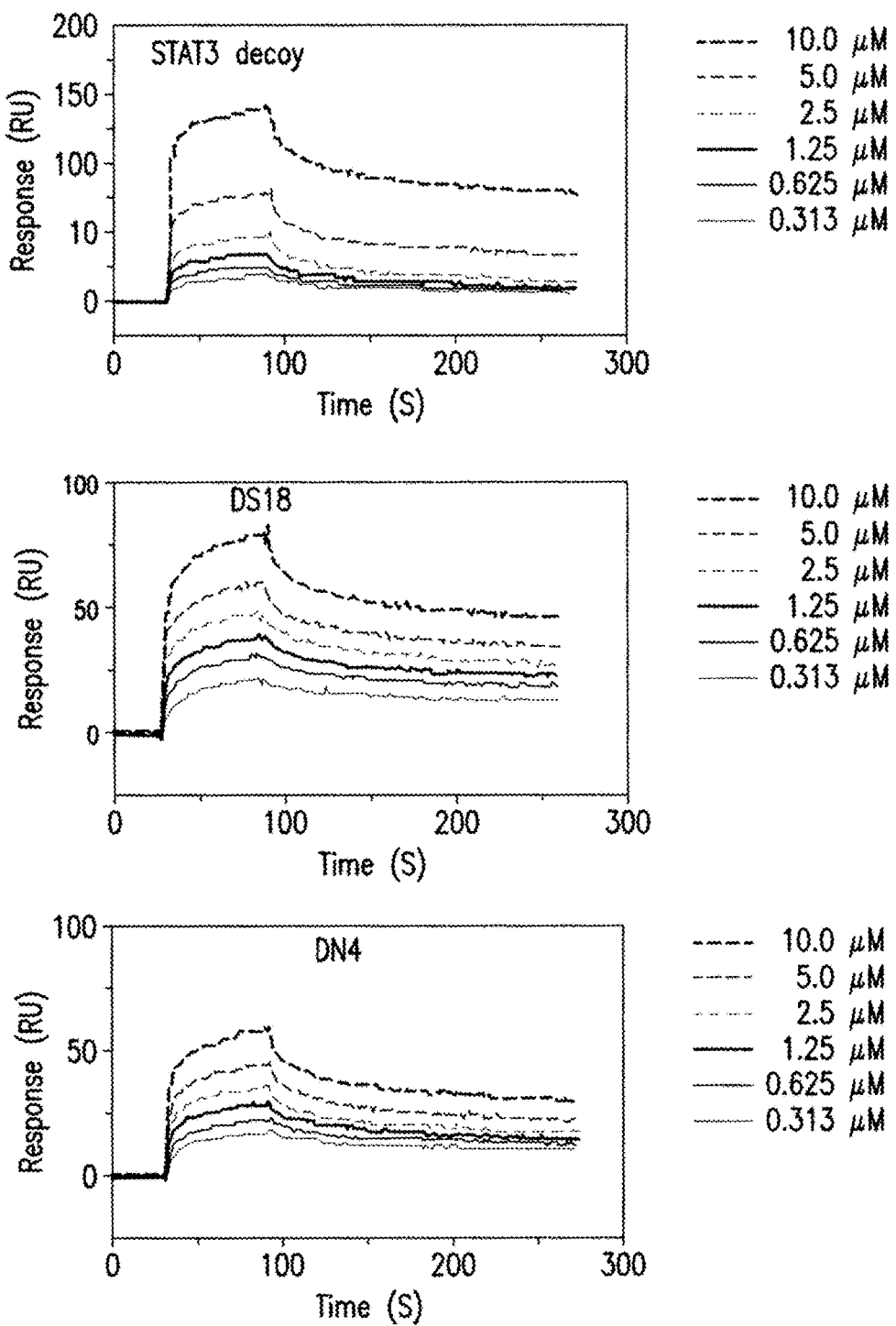
FIG. 20. Depicts binding affinities of STAT3 decoy, DN4 and DS18 to pSTAT3 protein. The response of STAT3 decoy, DN4 and DS18 in different concentrations to pSTAT3 immobilized on the CM5 chip is shown.

To determine the specific binding affinities of the parent and the modified decoys (DN4 and DS18) to the pSTAT3 protein, surface plasmon resonance (SPR) analyses were performed using a BIAcore 3000 instrument (GE Healthcare, Piscataway, N.J.). All buffer and sample solutions were filtered and degassed prior to each run, with more optimal pH and instrument parameters determined empirically. The pSTAT3 protein at 10 μg/ml in 10 mM sodium acetate buffer (pH 4.0), was immobilized on freshly activated chip surface. Phosphorylated STAT3 protein was coupled on carboxymethylated dextran matrix (CM5) chips following standard protocols. Unreacted sites on the chip surface were blocked using 1.0 M ethanolamine-HCl (pH 8.5). Binding of STAT3 decoy, DN4 and DS18 to pSTAT3 protein were determined at several concentrations such as 0.308 μM 0.625 μM, 1.25 μM, 2.5 μM 5.0 μM and 10.0 μM of analyte solutions, at a flow rate of 30 μL/min in a running buffer (20 mM HEPES, pH 7.0, 200 mM NaCl, 10 mM MgCl$_2$). Results are shown in FIG. 20. The amount of STAT3 decoy bound to pSTAT3 increased directly with increasing concentrations of STAT3 decoy.

Example 7: Internalization of Modified STAT3 Decoys Assay

The HNSCC cell line, UM-SCC1, was transfected in the presence of OPTIMEM and lipofectamine 2000 (Invitrogen, Carlsbad, Calif.), with 10 nM 5'carboxyfluorescein (FAM)-labeled STAT3 decoy, FAM-DN4 or FAM-DS18. Cells transfected with saline (vehicle) served as a control. After 24 hours, cells were washed three times with PBS and imaged with confocal microscopy to determine internalization of the STAT3 decoy, DN4 and DS18.

Figure 21:
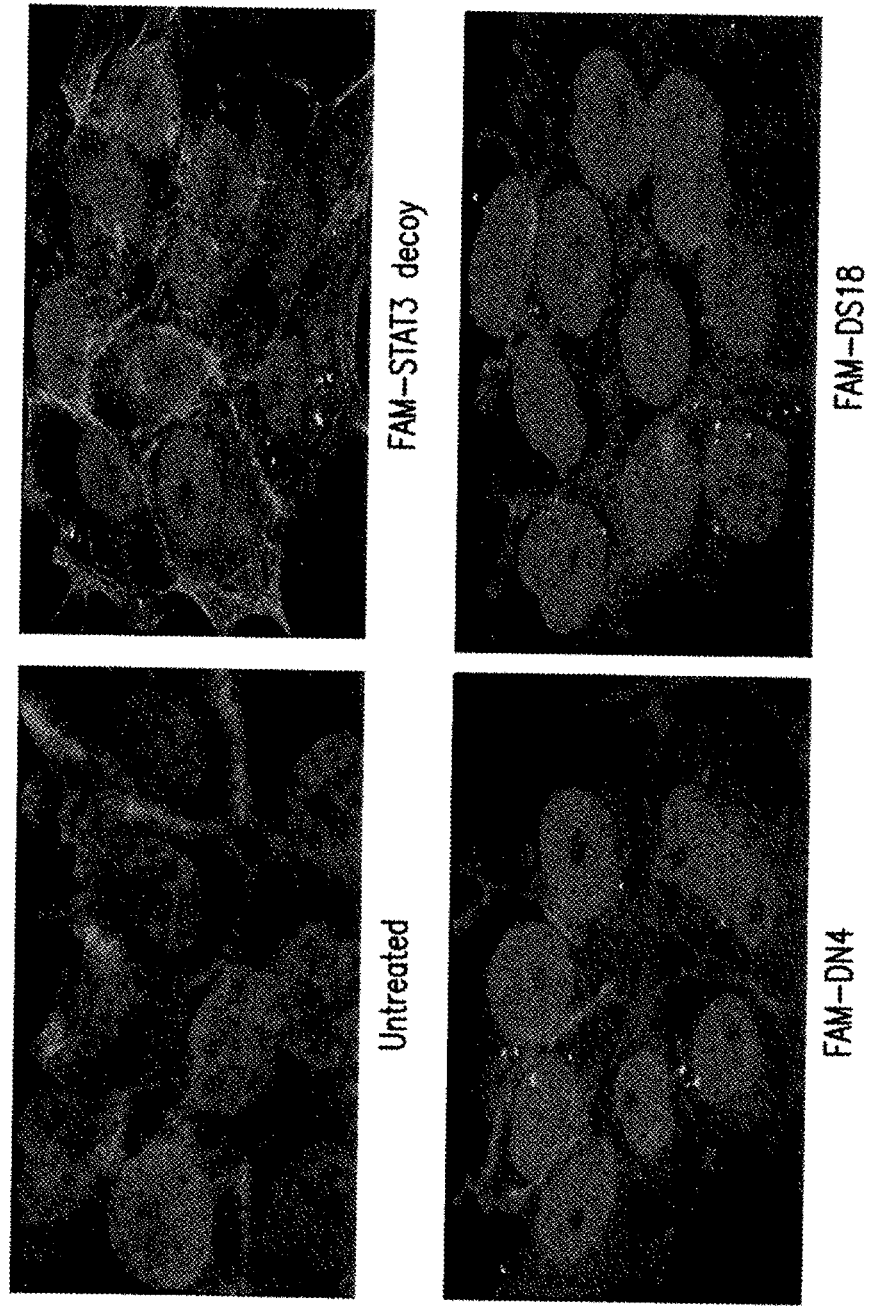
FIG. 21. Depicts incorporation of STAT3 decoy, DN4 and DS18 in UM-SCC1 cells using confocal microscopy. The white granular spots representing the decoys can be seen within the cells.

Results are shown in FIG. 21. The white granular spots representing the decoys can be seen within the cells. The modified STAT3 decoys (DN4 and DS18) showed uptake into head and neck cancer cells similar to the parent STAT3 decoy.

Example 8: In Vitro Modulation of Target Gene Expression

To determine the effects of the modified decoys on STAT3 target gene expression, UM-SCC1 cells were treated with DS18 at the $EC_{50}$ concentration (23.9 nM). After 4 hours, the transfection media was replaced with DMEM containing 10% serum. After 72 hours, whole cell lysates were extracted and subjected to immunoblotting for cyclin D1 and Bcl-$X_L$. β-tubulin was used as a loading control.

Figure 22:
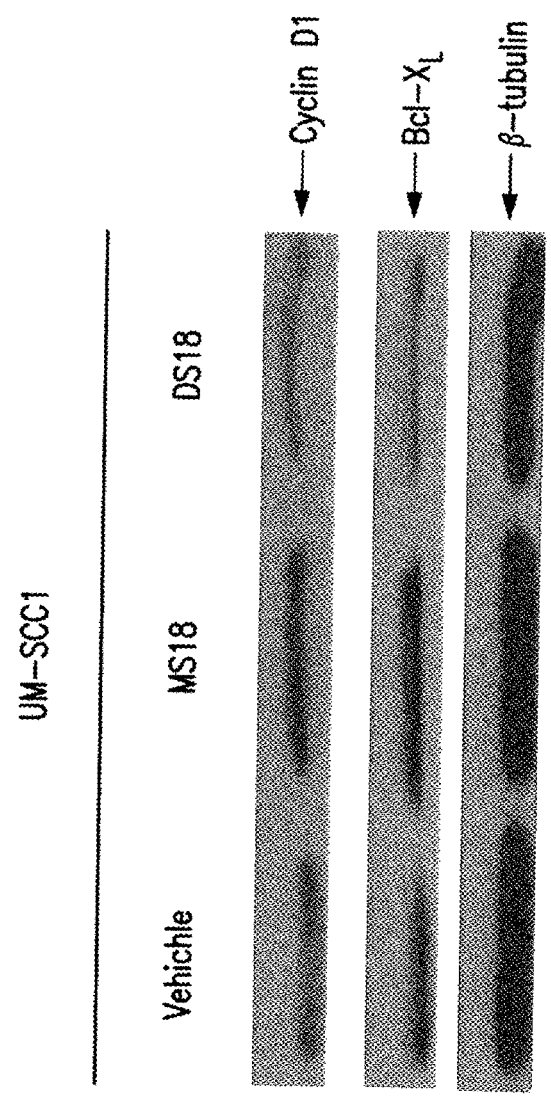
FIG. 22. Depicts down modulation of STAT3 target genes in UM-SCC1 cells treated with DS18. Western analyses of UM-SCC1 cells treated with DS18 at its $EC_{50}$ concentration or the same concentration of MS18. After 72 hours, cells were harvested and 40 μg protein was run on a 10% gel to determine cyclin D1 and Bcl-$X_L$ expression. β-tubulin was used as a loading control.

Results are shown in FIG. 22. The modified decoys DN4 and DS18 have shown in vitro potency in the low nanomolar range and have also demonstrated down modulation of STAT3 target genes.

Example 9: In Vivo Xenograft Tumor Gene Expression

Figure 23:
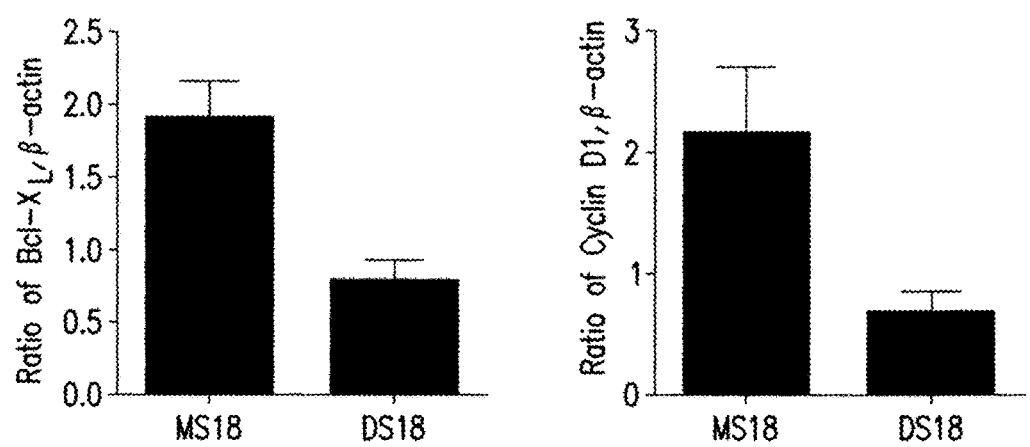
FIG. 23. Illustrates that DS18 modulates target gene expression in xenograft tumors at 24 hours. The bar graph is a quantitative representation of the expression of Bcl-$X_L$ and cyclin D1 relative to β-actin.

Female athymic nude mice nu/nu (4~6 weeks old; 20 g; Harlan Sprague-Dawley) were inoculated with UM-SCC1 cells (1.2×106 cells) and after 8 days when the tumors were palpable (3-4 mm3), mice (5 per group) were treated with a single intravenous injection of DS18 or MS18 (100 μg) via the tail vein. After 24 hours, tumors were harvested and Western blot analyses were performed on the tumor samples for Bcl-$X_L$ and cyclin D1. β-actin was used to assess protein loading. Results are shown in FIG. 23 where the bar graph is a quantitative representation of the expression of Bcl-$X_L$ and cyclin D1 relative to β-actin level. A single intravenous injection of DS18 caused a decrease in cyclin D1 and Bcl-$X_L$ in HNSCC xenograft tumors generated from UM-SCC1 cells, indicating that STAT3 decoy modified with 18-atom hexa-ethyleneglycol spacers (DS18) exhibits in vivo activity following systemic administration. Thus, DS18 and other modified STAT3 decoys represent potential therapeutic agents for modulating expression of STAT3 target genes in vivo in tumors.

CONCLUSIONS

The modified STAT3 decoys were tested for serum nuclease degradation, melting temperature, binding to pSTAT3 protein, uptake and biologic activity. For example, DN4 is stable up to 4 hours and DS18 up to 3.5 hours compared with the parent STAT3 decoy, which is resistant only up to 1.5 hours. The melting temperature demonstrated increased thermal stability for all the modified decoys compared to the parent STAT3 decoy. Also, the DN4 and DS18 modified decoys bound to recombinant pSTAT3 protein similarly to the parent decoy, and inhibited head and neck cancer cell proliferation in vitro at nanomolar concentrations.

These results indicate that modified STAT3 decoys have improved features in terms of stability and potential activity compared to the parent STAT3 decoy. For example, the binding efficiencies of DN4 and DS18 to pSTAT3 protein is highly comparable to the parent STAT3 decoy and their incorporation into HNSCC cells is also very similar. Stability in terms of thermal denaturation have shown increased melting temperature for DN4 and DS18 as compared to the parent STAT3 decoy. Linking the sense and the antisense strand of the STAT3 decoy by a tetra-nucleotide hairpin or an 18-atom hexa-ethyleneglycol spacer resulted in further improvement in oligonucleotide biostability. Also, the modified decoys DN4 and DS18 exhibit in vitro potency in the low nanomolar range and also caused downmodulation of STAT3 target genes. Furthermore, a single intravenous injection of DS18 resulted in downmodulation of cyclin D1 and Bcl-$X_L$ in HNSCC xenograft tumors generated from UM-SCC1 cells compared to injection of tumor-bearing mice injected with the mutant control MS18. These findings indicate that modified STAT3 decoys, including STAT3 decoys modified with 18-atom hexa-ethyleneglycol spacers (DS18), have significant potential as therapeutic agents to manipulate gene expression and thus have profound clinical relevance.

Various publications are cited herein, the contents of which are hereby incorporated by reference in their entireties.

What is claimed:

1. A cyclic double-stranded STAT3 oligonucleotide decoy, wherein (i) the decoy comprises a double-stranded oligonucleotide, or an analog thereof, having the sequence 5'-($N_6$-)$_n$CA$N_1$TTC$N_2$C$N_3$T$N_4$A$N_5$TC-($N_7$-)$_m$-3' (SEQ ID NO:1), wherein $N_3$ is G; $N_1$, $N_2$, $N_4$ and $N_5$ are A, T, G or C; one, two, three or all of the following conditions are met: $N_1$ is T; $N_2$ is C; $N_4$ is A and $N_5$ is A; and $N_6$ and $N_7$ are A, T, G or C and n and m are independently 0-50; (ii) the two strands are joined at the ends by chemical linkers; (iii) the decoy binds to STAT3 protein under physiologic conditions and interferes with STAT3 binding to its target sequence; and (iv) the decoy has a serum half-life of greater than about 4 hours.

2. The STAT3 oligonucleotide decoy of claim 1, wherein the oligonucleotide comprises the sequence 5'-CATTTCCCGTAAATC-3' (SEQ ID NO:30).

3. The STAT3 oligonucleotide decoy of claim 1, wherein $N_2$ is a pyrimidine.

4. The STAT3 oligonucleotide decoy of claim 1, wherein at least two of the following are met: $N_1$ is T; $N_2$ is C; $N_4$ is A; and $N_5$ is A.

5. The STAT3 oligonucleotide decoy of claim 1, wherein the chemical linker is a chemical structure comprising a carbon spacer.

6. The STAT3 oligonucleotide decoy of claim 5, wherein the carbon spacer has 18 carbons.

7. The STAT3 oligonucleotide decoy of claim 5, wherein the carbon spacer comprises an ethylene glycol spacer, optionally wherein the ethylene glycol is a hexaethylene glycol.

8. A pharmaceutical composition comprising a pharmaceutically acceptable carrier and a cyclic double-stranded STAT3 oligonucleotide decoy, wherein (i) the decoy comprises a double-stranded oligonucleotide, or an analog thereof, having the sequence 5'-($N_6$-)$_n$CA $N_1$TTC$N_2$C $N_3$T $N_4$A $N_5$TC-($N_7$-)$_m$-3' (SEQ ID NO:1), wherein $N_3$ is G; $N_1$, $N_2$, $N_4$ and $N_5$ are A, T, G or C; one, two, three or all of the following conditions are met: $N_1$ is T; $N_2$ is C; $N_4$ is A and $N_5$ is A; and $N_6$ and $N_7$ are A, T, G or C and n and m are independently 0-50; (ii) the two strands are joined at the ends by chemical linkers; (iii) the decoy binds to STAT3 protein under physiologic conditions and interferes with STAT3 binding to its target sequence; and (iv) the decoy has a serum half-life of greater than about 4 hours.

9. The pharmaceutical composition of claim 8, further comprising an anticancer agent.

10. The composition of claim 8, formulated as a parenteral dosage form or an intravenous dosage form.

11. The composition of claim 8, wherein the decoy is contained within a microbubble.

12. The composition of claim 8, wherein the decoy is associated with a peptide transduction domain, optionally wherein the peptide transduction domain is TAT.

13. A method of inhibiting growth of a cancer in which STAT3 is activated in a patient, comprising administering to the patient an amount of a cyclic double-stranded STAT3 oligonucleotide decoy effective to inhibit growth of a cancer in a patient, thereby inhibiting growth of the cancer in the patient; wherein the oligonucleotide decoy (i) comprises a double-stranded oligonucleotide having the sequence 5'-($N_6$-)$_n$CA$N_1$TTC$N_2$C$N_3$T$N_4$A$N_5$TC-($N_7$-)$_m$-3' (SEQ ID NO: 1), wherein $N_3$ is G; $N_1$, $N_2$, $N_4$ and $N_5$ are A, T, G or C; one, two, three or all of the following conditions are met: $N_1$ is T; $N_2$ is C; $N_4$ is A and $N_5$ is A; and $N_6$ and $N_7$ are A, T, or C and n and m are independently 0-50; (ii) the two strands are joined at the ends by two chemical linkers; (iii) the decoy binds to STAT3 protein under physiologic conditions and interferes with STAT3 binding to its target sequence; and (iv) the decoy has a serum half-life of greater than about 4 hours.

14. The method of claim 13, comprising administering to the patient a second anticancer therapy comprising one or both of a radiation therapy and treating the patient with an anticancer agent.

15. The methods of claim 14, wherein the anticancer therapy comprises an epidermal growth factor receptor (EGFR) antagonist, optionally wherein the EGFR antagonist is cetuximab.

16. The method of claim 13, wherein the cancer is selected from the group consisting of multiple myeloma, HTLV-1 dependent leukemia, acute myelogenous leukemia, large granular lymphocyte leukemia, lymphoma, EBV-related Burkitt's lymphoma, mycosis fungoides, cutaneous T-cell lymphoma, non-Hodgkins lymphoma, anaplastic large-cell lymphoma, breast cancer, melanoma, ovarian cancer, lung cancer, pancreatic cancer, prostate cancer and squamous cell carcinoma, optionally wherein the squamous cell carcinoma is squamous cell carcinoma of the head and neck.

17. The method of claim 13, wherein the STAT3 oligonucleotide decoy comprises the sequence 5'CATTTCCCGTAAATC-3' (SEQ ID NO:30).

18. The method of claim 13, wherein, in the STAT3 oligonucleotide decoy, $N_2$ is a pyrimidine or at least two of the following are met: $N_1$ is T; $N_2$ is C; $N_4$ is A; and $N_5$ is A.

19. The method of claim 13, wherein, in the STAT3 oligonucleotide decoy, the chemical linker is a chemical structure comprising a carbon spacer.

20. The method of claim 19, wherein the carbon spacer comprises an ethylene glycol spacer, optionally wherein the ethylene glycol is a hexaethylene glycol.

* * * * *